(12) United States Patent
Womack et al.

(10) Patent No.: US 11,667,869 B2
(45) Date of Patent: Jun. 6, 2023

(54) ENOL ETHER PRO PERFUME

(71) Applicant: FIRMENICH SA, Satigny (CH)

(72) Inventors: Gary B. Womack, Plainsboro, NJ (US); Brinda Indradas, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/981,152

(22) PCT Filed: Jun. 20, 2019

(86) PCT No.: PCT/EP2019/066356
§ 371 (c)(1),
(2) Date: Sep. 15, 2020

(87) PCT Pub. No.: WO2019/243501
PCT Pub. Date: Dec. 26, 2019

(65) Prior Publication Data
US 2021/0115354 A1 Apr. 22, 2021

Related U.S. Application Data

(60) Provisional application No. 62/689,017, filed on Jun. 22, 2018.

(30) Foreign Application Priority Data

Aug. 13, 2018 (EP) .................................... 18188738

(51) Int. Cl.
*C11B 9/00* (2006.01)
*A61K 8/35* (2006.01)
*A61Q 13/00* (2006.01)
*C07C 43/166* (2006.01)

(52) U.S. Cl.
CPC .............. *C11B 9/0061* (2013.01); *A61K 8/35* (2013.01); *A61Q 13/00* (2013.01); *C07C 43/166* (2013.01); *C11B 9/0053* (2013.01)

(58) Field of Classification Search
CPC .................................................. C11B 9/0061
See application file for complete search history.

(56) References Cited

FOREIGN PATENT DOCUMENTS

WO 2012085287 A1 6/2012
WO 2014180791 A1 11/2014

OTHER PUBLICATIONS

Liu, et al. ("Regiodivergent radical oxidative coupling of vinyl ethers with dithiane by copper or iron catalysis", Organic Chemistry Frontiers, Issue 11, 2017). (Year: 2017).*
International Search Report and Written Opinion for corresponding PCT/EP2019/066356 dated Sep. 5, 2019, 10 pages.
Makoto Tokunaga et al. "Copper-catalized Oxidative Cleavage of Carbon-carbon Double Bond of Enol Ethers with Molecular Oxygen". Journal of Organometallic Chemistry., vol. 690, No. 23, Published Nov. 1, 2005.
Tatsya Kanno et al. "Oxygenation of Aromatic Vinal Ethers. A Noticeable Formation of Epoxides and Reaction Mechanism". Bulletin of the Chemical Society of Japan, vol. 54, No. 8, pp. 2330-2336, Published 1981.
Lee H Y "Microencapsulation of Fragrant Oil via in Situ Polymerization: Effects of pH and Melamine-formaldehyde Motor Ratio" Journal of Microencapsulation, 19(5) 559-569, Published 2002.
Dietrich et al., "Amino Resin Microcapsules IV" Acta Polymerica, 41, No. 2, pp. 91-95, Published 1990.
Dietrich et al., "Amino Resin Microcapsules II" Acta Polymerica, 40, No. 5, pp. 325-331, Published 1989.
Dietrich et al., "Amino Resin Microcapsules I" Acta Polymerica, 40, No. 4, pp. 243-251, Published 1989.
Dietrich et al., "Amino Resin Microcapsules III" Acta Polymerica, vol. 40, No. 11, pp. 683-690, Published 1989.

\* cited by examiner

*Primary Examiner* — Arrie L Reuther
(74) *Attorney, Agent, or Firm* — Armstrong Teasdale LLP

(57) ABSTRACT

Described herein are properfume compounds. Also described herein is a method to release a compound being a ketone or aldehyde, a formate ester and/or an alcohol by exposing a properfume compound to an environment wherein it is oxidized. Also described herein is a perfuming composition and a perfume consumer product comprising at least one properfume compound.

8 Claims, No Drawings

ENOL ETHER PRO PERFUME

CROSS-REFERENCE TO RELATED APPLICATIONS

This application is a U.S. National Phase Application of PCT/EP2019/066356, filed Jun. 20, 2019, which claims the benefit of priority to U.S. Provisional Patent Application No. 62/689,017, filed Jun. 22, 2018, and which claims the benefit of priority to European Patent Application No. 18188738.1, filed Aug. 13, 2018, the entire contents of which are hereby incorporated by reference herein.

TECHNICAL FIELD

The present invention relates to compounds of formula (I) as properfume compounds. In particular, the present invention relates to a method to release a compound being a ketone or aldehyde of formula (II), a formate ester of formula (III) and/or an alcohol of formula (IV), by exposing the compound of formula (I) to an environment wherein it is oxidized. Moreover, the present invention relates to a perfuming composition and a perfume consumer product comprising at least one compound of formula (I).

BACKGROUND

The perfume industry has a particular interest for compositions or additives which are capable of prolonging or enhancing the perfuming effect of a mixture of several fragrances at the same time over a certain period of time. It is particularly desirable to obtain long-lasting properties for standard perfumery raw materials which are too volatile or have a poor substantivity by themselves, or which are only deposited in a small amount onto the surface of the final application. Furthermore, some of the perfumery ingredients, especially aldehydes, are unstable and need to be protected against slow degradation prior to their use. Long-lasting perfumes are desirable for various applications, as for example fine or functional perfumery or cosmetic preparations. The washing and softening of textiles is a particular field in which there is a constant need to enable the effect of active substances, in particular perfumes, or perfuming compositions, to be effective for a certain period of time after washing, softening and drying. Indeed, many active substances which are particularly suitable for this type of application are known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

It has now surprisingly found that enol ether compounds according to the present invention solve the above-mentioned problems and are capable of efficiently releasing a compound being a ketone or aldehyde of formula (II), a formate ester of formula (III) and/or an alcohol of formula (IV). To the best of our knowledge, only structural analogues have been reported in prior arts such as WO2014/180791 disclosing allyl ether derivatives.

DESCRIPTION OF THE INVENTION

Olfaction is a complex and dynamic process, and controlling the release profile of volatile fragrance compounds may maximize the impact of fragrance formulations and enrich the sensorial experience. Profragrances, such as the compounds of the present invention add a dimension of control and long-lastingness to the release profile of highly volatile perfumery raw materials (PRMs).

Without intending to be limited to any particular theory, the compounds of the present invention may achieve their effect on the olfactive properties of a perfuming composition by tethering the PRM to a molecular anchor and requiring a specific reaction mechanism under certain environmental conditions to release the volatile PRM from this anchor. In the present invention, the binary release of two PRMs is prompted by oxidation when the profragrance is exposed to the oxygen in ambient air.

The first object of the present invention is a method to release from a precursor compound, compounds selected from the group consisting of
  a) a ketone or aldehyde of formula

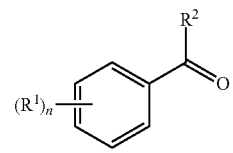

(II)

wherein n represent an integer between 0 and 5;
$R^1$, simultaneously or independently, represents at least one substituent of the aromatic ring and are a hydroxyl group, a $C_{1-6}$ alkyl group, a $C_{1-6}$ alkoxy group or a RCOO, a ROCO group wherein R is a hydrogen atom or a $C_{1-4}$ alkyl group; or two adjacent $R^1$, when taken together, represent a —O—$(CH_2)_m$—O— wherein m is 1 or 2 or form a $C_{5-10}$ saturated or unsaturated ring optionally substituted by one or more than one hydroxyl group, one or more than one $C_{1-3}$ alkyl group and/or one or more than one $C_{1-3}$ alkoxy group;
$R^2$ represents a hydrogen atom, a $C_{1-6}$ alkyl group or a $C_{6-10}$ aromatic group optionally substituted by a hydroxyl group, a $C_{1-3}$ alkyl group, a $C_{1-3}$ alkoxy group, a RCOO or a ROCO group wherein R is, independently from each other, a hydrogen atom or a $C_{1-4}$ alkyl group;
  b) a formate ester of formula

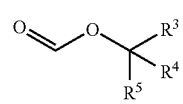

(III)

wherein $R^3$, $R^4$ and $R^5$ represent, simultaneously or independently, a hydrogen atom, or a $C_{1-18}$ hydrocarbon group optionally comprising one to three oxygen atoms; or $R^3$ and $R^4$, represent, when taken together, a $C_{3-18}$ hydrocarbon group optionally comprising one to three oxygen atoms; and
  c) an alcohol of formula

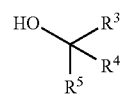

(IV)

wherein $R^3$, $R^4$ and $R^5$ have the same meaning as defined above; wherein at least one of the compounds of formula (II), (III) or (IV) is an active compound,
wherein the precursor compound comprises a compound of formula (I)

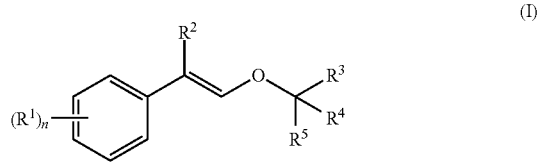

wherein n, $R^1$, $R^2$, $R^3$, $R^4$ and $R^5$ have the same meaning as defined above by exposing the precursor compound of formula (I) to an environment wherein the compound is oxidized; i.e. ambient conditions.

The terms "active compound", "active volatile compound", "active volatile aldehyde, ketone, formate ester and/or alcohol" or the similar, are understood as aldehyde, ketone, formate ester and/or alcohol compounds being capable of bringing a benefit or effect into its surrounding environment. In particular the "active compound" is selected from the group consisting of a perfuming ingredient, flavoring ingredient, malodor counteracting ingredient and insect repellent or attractant ingredient. Therefore, to be considered as an "active compound" the compound has to possess at least one property which renders it useful as a perfuming ingredient, as a malodor counteracting ingredient, a flavoring ingredient, and/or as an insect repellent or attractant.

The term "perfuming ingredient" is understood as a compound which is used as an active ingredient in perfuming preparations or compositions in order to impart a hedonic effect. In other words, a compound to be considered as being a perfuming ingredient, must be recognized by a skilled person in the art of perfumery as being able to impart or modify in a positive or pleasant way the odor of a composition, and not just as having an odor. The term "flavoring ingredient" is understood to as being capable of imparting a taste sensation to the taster's pallet. The term "malodor counteracting ingredient" is understood as being capable of reducing the perception of malodor, i.e. of an odor that is unpleasant or offensive to the human nose. The term "insect attractant or repellent" is understood as a compound having a positive or negative effect on insects. Examples of insect attractant or repellent ingredients can be found in reference texts or in other works of a similar nature as for example: A. M. El-Sayed, The Pherobase 2005, http://www.pherobase.net.

According to the above and below mentioned embodiments of the invention, the method according to the present invention is particularly useful when the active compound is a perfuming ingredient, i.e. a perfuming aldehyde, ketone, formate ester and/or alcohol. A "perfuming aldehyde, ketone, formate ester and/or alcohol" is a compound, which is of use in the perfumery industry, i.e. a compound which is used as active ingredient in perfuming preparations or compositions in order to impart a hedonic effect. In other words, such an aldehyde, ketone, formate ester and/or alcohol, to be considered as being a perfuming one, must be recognized by a person skilled in the art of perfumery as being able to impart or modify in a positive or pleasant way the odor of a composition, and not just as having an odor. The perfuming aldehyde, ketone, formate ester and/or alcohol can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

Herein described, the terms "perfuming aldehyde, ketone, formate ester and/or alcohol" are also referred to as "perfuming compounds".

Practically, the invention is carried out exactly in the same manner, independently of the exact properties of the active aldehyde, ketone, formate ester or alcohol. Therefore, it is understood that, even if the invention will be further illustrated herein below with a specific reference to "perfuming compounds", the below embodiments are also applicable to other active aldehyde, ketone, formate ester and/or alcohol (i.e. it is possible to replace the expression "perfuming" with "flavoring", "malodor counteracting", "insect attractant" or with "insect repellent" for instance).

The term "hydrocarbon group" is understood as a group consisting of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of the type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of the topologies or being saturated or unsaturated, as explained above. Similarly, in all the embodiments of the invention, when a group is mentioned as being in the form of one type of saturation or unsaturation, (e.g. alkyl), it is meant that the group can be in any type of topology (e.g. linear, cyclic or branched) or having several moieties with various topologies. The terms "arylalkyl" has the normal meaning in the art, i.e. it is an acyclic alkyl group wherein one hydrogen atom is substituted with an aryl group. The term "alicyclic group" has the normal meaning in the art; i.e. it is an organic compound that is both aliphatic and cyclic and which contains one or more all-carbon rings which may be either saturated or unsaturated.

The expression "comprising one to three oxygen atoms", or the similar, is understood as including functional groups such as for examples ethers, acetals, esters, aldehydes, ketones, carboxylates or alcohols.

The expression "substituted by one or more than one hydroxyl group, one or more than one $C_{1-3}$ alkyl group and/or one or more than one $C_{1-3}$ alkoxy group", or the similar, is understood as being substituted by 1 to 4 hydroxyl groups, 1 to 6 $C_{1-3}$ alkyl groups and/or 1 to 6 $C_{1-3}$ alkoxy groups, particularly as being substituted by 1 to 3 hydroxyl groups, 1 to 5 $C_{1-3}$ alkyl groups and/or 1 to 3 $C_{1-3}$ alkoxy groups.

According to any one of the above embodiments, the compounds of formula (I) and (II) are defined wherein n is 0, 1, or 2. Preferably, n may be 0 or 1.

According to any embodiments, the compounds of formula (I) and (II) are defined wherein $R^1$, simultaneously or independently, represents a hydroxyl group, a $C_{1-4}$ alkyl group or a $C_{1-3}$ alkoxy group; or two adjacent $R^1$ represent, when taken together, a —O—CH$_2$—O— group, a —(CH$_2$)$_4$— group, —(CH)$_4$— group. Preferably, the compounds of formula (I) and (II) are defined wherein $R^1$, simultaneously or independently, represents a methyl group, an ethyl group, a methoxy group, an ethoxy group; or two adjacent $R^1$ represent, when taken together, a —(CH$_2$)$_4$— group or —(CH)$_4$— group.

According to any embodiments, the compounds of formula (I) and (II) are defined wherein $R^2$ represents a hydrogen atom, a $C_{1-3}$ alkyl group or a phenyl group. Preferably, $R^2$ may represent a hydrogen atom, a methyl or a phenyl group.

According to any one of the above embodiments, $R^3$, $R^4$ and $R^5$ groups comprise at least 5 carbon atoms.

According to any embodiments, the compound of formula (III) is derived from an active alcohol of formula $(R^3)(R^4)(R^5)$COH having a molecular weight comprised between 80 and 230 g/mol and being a $C_{5-18}$ compound.

According to any embodiments, the compound of formula (IV) is an active alcohol of formula $(R^3)(R^4)(R^5)$COH having a molecular weight comprised between 80 and 230 g/mol and being a $C_{5-18}$ compound.

According to any embodiments, the compounds of formula (I), (III) and (IV) are defined wherein $R^3$ represents a $C_{2-18}$ hydrocarbon group optionally comprising one to three oxygen atoms. Preferably, the compounds of formula (I), (III) and (IV) are defined wherein $R^3$ may represent a $C_{4-10}$ linear, branched or cyclic alkyl, alkenyl or alkadienyl group, a phenyl, a benzyl, a $C_{7-16}$ arylalkyl or a styryl group optionally substituted by a hydroxyl, a $C_{1-3}$ alkyl or a $C_{1-3}$ alkoxy group, a phenoxymethyl group or a $C_{8-15}$ saturated or unsaturated alicyclic group comprising optionally an ether functional group. Preferably, $R^3$ may represent a $C_{4-10}$ linear, branched or cyclic alkyl or alkenyl group, a phenyl, a benzyl or a $C_{7-10}$ arylalkyl group optionally substituted by a hydroxyl, a $C_{1-3}$ alkyl or a $C_{1-3}$ alkoxy group, a phenoxymethyl group or a $C_{8-15}$ saturated or unsaturated alicyclic group comprising optionally an ether functional group. Preferably, $R^3$ may represent a $C_{4-10}$ linear, branched or cyclic alkyl or alkenyl group, a phenyl, a benzyl or a $C_{7-10}$ arylalkyl group optionally substituted by a hydroxyl, a $C_{1-3}$ alkyl group or a $C_{1-3}$ alkoxy group or a phenoxymethyl group. Even more preferably, $R^3$ may represent a $C_{4-10}$ linear, branched or cyclic alkyl or alkenyl group, a phenyl, a benzyl or a phenoxymethyl group.

According to any embodiments, $R^4$ and $R^5$ may represent, simultaneously or independently, a hydrogen atom or a $C_{1-6}$ alkyl group or a $C_{2-6}$ alkenyl group. Preferably, $R^4$ and $R^5$ may represent, simultaneously or independently, a hydrogen atom or a $C_{1-6}$ alkyl group. Preferably, $R^4$ and $R^5$ may represent, simultaneously or independently, a hydrogen atom or a $C_{1-3}$ alkyl group. Preferably, $R^4$ may represent a hydrogen atom or a $C_{1-3}$ alkyl group and $R^5$ may represent a hydrogen atom or a methyl group. Even more preferably, $R^4$ may represent a hydrogen atom or a methyl group and $R^5$ may represent a hydrogen atom or a methyl group.

According to any embodiments, $R^3$ and $R^4$, when taken together, may represent a $C_{5-12}$ linear or branched alkanediyl or alkenediyl group or a $C_{5-12}$ alicyclic group. Preferably, $R^3$ and $R^4$, when taken together, may represent a $C_{8-12}$ linear or branched alkanediyl or alkenediyl group. Even more preferably, $R^3$ and $R^4$, when taken together, may represent a $C_{8-12}$ linear or branched alkanediyl group.

According to any embodiments, the aldehyde or ketone of formula (II), the formate ester of formula (III) and/or the active alcohol of formula (IV) are perfuming ingredients. For a person skilled in the art it is also evident that compounds according to the present invention are inherently volatile compounds. Acording to any embodiment at least one of the compounds of formula (II), (III) or (IV) is a perfuming ingredient. Preferably, at least two of the compounds of formula (II), (III) or (IV) are perfuming ingredients The aldehyde, ketone, formate ester and/or alcohol may be advantageously characterized by a vapor pressure above 1.0 Pa, as obtained by calculation using the software EPIwin v. 3.10 (2000, available at the US Environmental Protection Agency). According to another embodiment, the vapor pressure of the aldehyde, ketone, formate ester and/or alcohol may be above 5.0, or even above 7.0 Pa. In some embodiments, the vapor pressure of the aldehyde, ketone, formate ester and/or alcohol may be below 1.0 Pa.

In one embodiment, the compound of formula (I) is non-volatile. The compound of formula (I) may be advantageously characterized by a vapor pressure below 0.01 Pa, as obtained by calculation using the software EPIwin v. 3.10 (2000, available at the US Environmental Protection Agency). According to one embodiment, the vapor pressure is below 0.001 Pa.

According to any embodiments, the ketone or aldehyde of formula (II) are selected from the group consisting of benzaldehyde, 4-methylbenzaldehyde, 4-ethylbenzaldehyde, 4-isopropylbenzaldehyde, 4-(tert-butyl) benzaldehyde, 4-methoxybenzaldehyde, 3,4-dimethoxybenzaldehyde, benzo[d][1,3]dioxole-5-carbaldehyde, vanillin, 3-ethoxy-4-hydroxybenzaldehyde, 4-formyl-2-methoxyphenyl acetate, 4-formyl-2-methoxyphenyl isobutyrate, 3,5,5,6,7,8,8-heptamethyl-5,6,7,8-tetrahydronaphthalene-2-carbaldehyde, acetophenone, propiophenone, 2-methyl-1-phenylpropan-1-one, p-methylacetophenone, p-isopropylacetophenone, p-tert-butylacetophenone, p-methoxyacetophenone, benzophenone, 1-(5,6,7,8-tetrahydronaphthalen-2-yl)ethan-1-one, 1-(naphthalen-2-yl)ethan-1-one, 1-(p-tolyl)propan-1-one, 1-(1,1,2,3,3,6-hexamethyl-2,3-dihydro-1H-inden-5-yl)ethan-1-one, 1-(3,5,5,6,8,8-hexamethyl-5,6,7,8-tetrahydronaphthalen-2-yl)ethan-1-one, 1-(6-tert-butyl-1,1-dimethyl-4-indanyl)-1-ethanone, (3-isopropyl-1,1,2,6-tetramethyl-5-indanyl)-1-ethanone, 4-tert-butyl-2,6-dimethyl-1-acetophenone and 1-(5,6,7,8-tetrahydro-3,5,5,6,8,8-hexamethyl-2-naphthalenyl)-1-ethanone.

According to any embodiments, the ketone or aldehyde of formula (II) is selected from acetophenone, benzaldehyde, benzophenone, p-methylacetophenone, p-methoxyacetophenone, 1-(naphthalen-2-yl)ethan-1-one, 1-(5,6,7,8-tetrahydronaphthalen-2-yl)ethan-1-one, propiophenone, 1-phenylbutan-1-one, and 2-methyl-1-phenylpropan-1-one.

According to any embodiments, the formate ester of formula (III) are selected from the group consisting of phenethyl formate, 3,7-dimethyloct-6-en-1-yl formate, 2-phenoxyethyl formate, 1-((1RS,6SR)-2,2,6-trimethylcyclohexyl)hexan-3-yl formate, octan-3-yl formate, (1RS, 2SR,5RS)-2-isopropyl-5-methylcyclohexyl formate, 1-((2-(tert-butyl)cyclohexyl)oxy)butan-2-yl formate, 2,6-dimethyloct-7-en-2-yl formate, 3,7-dimethyloctan-3-yl formate, 2-methyl-1-phenylpropan-2-yl formate, 2,6-dimethylheptan-2-yl formate, methyl formate, ethyl formate, propyl formate, isopropyl formate, butyl formate, pentyl formate, 2-methylbutyl formate, 3-methylbutyl formate, butan-2-yl formate, 2-methylpropyl formate, cyclohexyl formate, hexyl formate, heptyl formate, octyl formate, nonyl formate, decyl formate, 3-octyl formate, benzyl formate, 3,7-dimethyloct-6-enyl formate, cinnamyl formate, 4-methoxybenzyl formate, (E)-3,7-dimethylocta-2,6-dien-1-yl formate, (Z)-3,7-dimethylocta-2,6-dien-1-yl formate, 2-hexenyl formate, 3-hexenyl formate, 3,5,5-trimethylhexyl formate, 2-phenylethyl formate, 2-(phenoxy)ethyl formate, 3-phenylpropyl formate, 3-methylbut-2-enyl formate, bornyl formate, isobornyl formate, 2-methyl-5-(prop-1-en-2-yl)cyclohex-2-en-1-yl formate, cedryl formate, cyclododecayl formate, decahydronaphthalen-2-yl formate, menthyl formate, 1-phenylethyl formate, 5-methyl-2-(prop-1-en-2-yl)cyclohexyl formate, 3a,4,5,6,7,7a-hexahydro-1H-4,7-methanoinden-5-yl formate, 3a,4,5,6,7,7a-hexahydro-1H-4,7-methanoinden-6-yl formate, 1-(3,3-dimethylcyclohexyl)ethyl formate, 2-methyl-1-phenylpropan-2-yl formate and 3,7-dimethylocta-1,6-dien-3-yl formate and 2,6-dimethylocta-2,7-dien-1-yl formate.

According to any embodiments, the formate ester (III) are selected from phenethyl formate, 3-hexenyl formate , octyl formate, decyl formate, 3,7-dimethyloct-6-en-1-yl formate, 2-phenoxyethyl formate, 1-((1RS,6SR)-2,2,6-trimethylcyclohexyl)hexan-3-yl formate, hexyl formate, benzyl formate, octan-3-yl formate, (1RS,2SR,5RS)-2-isopropyl-5-methylcyclohexyl formate, cyclododecayl formate, 1-(3,3-dimethylcyclohexyl)ethyl formate, 1-((2-(tert-butyl)cyclohexyl)oxy)butan-2-yl formate, 2,6-dimethyloct-7-en-2-yl formate, 3,7-dimethyloctan-3-yl formate, 2-methyl-1-phenylpropan-2-yl formate, 2,6-dimethylheptan-2-yl formate.

According to any embodiments, the alcohol is selected from the group consisting of 2-phenylethan-1-ol, octan-1-ol, hex-3-en-1-ol, 3,7-dimethyloct-6-en-1-ol, decan-1-ol, 2-phenoxyethan-1-ol, 1-((1RS,6SR)-2,2,6-trimethylcyclohexyl)hexan-3-ol, octan-3-ol, (1RS,2SR,5RS)-2-isopropyl-5-methylcyclohexan-1-ol, 1-((2-(tert-butyl)cyclohexyl)oxy)butan-2-ol, 2,6-dimethyloct-7-en-2-ol, 3,7-dimethyloctan-3-ol, 2-methyl-1-phenylpropan-2-ol, 2,6-dimethylheptan-2-ol, methanol, ethanol, propan-1-ol, propan-2-ol, butan-1-ol, pentan-1-ol, 2-methylbutan-1-ol, 3-methylbutan-1-ol, butan-2-ol, 2-methylpropan-1-ol, cyclohexanol, hexan-1-ol, heptan-1-ol, nonan-1-ol, phenylmethanol, 3,7-dimethyloct-6-en-1-ol, 3-phenylprop-2-en-1-ol, (4-methoxyphenyl)methanol, (E)-3,7-dimethylocta-2,6-dien-1-ol, (Z)-3,7-dimethylocta-2,6-dien-1-ol, hex-2-en-1-ol, 3,5,5-trimethylhexan-1-ol, 3-phenylpropan-1-ol, 3-methylbut-2-en-1-ol, 1,7,7-trimethylbicyclo[2.2.1]heptan-2-ol, 1,7,7-trimethylbicyclo[2.2.1]heptan-2-ol, 2-methyl-5-(prop-1-en-2-yl)cyclohex-2-en-1-ol, (3S,3aR,6R,7S,8aS)-3,6,8,8-tetramethyloctahydro-1H-3a,7-methanoazulen-3-ol, cyclododecanol, decahydronaphthalen-2-ol, 2-isopropyl-5-methylcyclohexan-1-ol, 1-phenylethan-1-ol, 5-methyl-2-(prop-1-en-2-yl)cyclohexan-1-ol, 3a,4,5,6,7,7a-hexahydro-1H-4,7-methanoinden-5-ol, 3a,4,5,6,7,7a-hexahydro-1H-4,7-methanoinden-6-ol, 1-(3,3-dimethylcyclohexyl)ethan-1-ol, 2-methyl-1-phenylpropan-2-ol, 3,7-dimethylocta-1,6-dien-3-ol and 2,6-dimethylocta-2,7-dien-1-ol.

According to any embodiments, the alcohol is selected from the group consisting of 2-phenylethan-1-ol, octan-1-ol, hex-3-en-1-ol, heptan-1-ol, nonan-1-ol, decan-1-ol, 2-phenoxyethan-1-ol, 1-((1RS,6SR)-2,2,6-trimethylcyclohexyl)hex an-3-ol, hexan-1-ol, phenylmethanol, octan-3-ol, 3,7-dimethyloct-6-en-1-ol, (1RS,2SR,5RS)-2-isopropyl-5-methylcyclohexan-1-ol, cyclododecanol, 1-(3,3-dimethylcyclohexyl)ethan-1-ol, 1-((2-(tert-butyl)cyclohexyl)oxy)butan-2-ol, 2,6-dimethyloct-7-en-2-ol, 3,7-dimethyloctan-3-ol, 2-methyl-1-phenylpropan-2-ol, and 2,6-dimethylheptan-2-ol.

According to any embodiments, the compound of formula (I) is selected from the group consisting of (1-(octyloxy)prop-1-en-2-yl)benzene, (1-(((Z)-hex-3-en-1-yl)oxy)prop-1-en-2-yl)benzene, (1-(decyloxy)prop-1-en-2-yl)benzene, (1-phenethoxyprop-1-en-2-yl)benzene, (1-((3,7-dimethyloct-6-en-1-yl)oxy)prop-1-en-2-yl)benzene, (1-(2-phenoxyethoxy)prop-1-en-2-yl)benzene, (1-((1-((1R,6S)-2,2,6-trimethylcyclohexyl)hexan-3-yl)oxy)prop-1-en-2-yl)benzene, (1-(hexyloxy)prop-1-en-2-yl)benzene, (1-(benzyloxy)prop-1-en-2-yl)benzene, (1-(octan-3-yloxy)prop-1-en-2-yl)benzene, (1-(((1R,2S,5R)-2-isopropyl-5-methylcyclohexyl)oxy)prop-1-en-2-yl)benzene, ((2-phenylprop-1-en-1-yl)oxy)cyclododecane, (1-(1-(3,3-dimethylcyclohexyl)ethoxy)prop-1-en-2-yl)benzene, (1-((1-((2-(tert-butyl)cyclohexyl)oxy)butan-2-yl)oxy)prop-1-en-2-yl)benzene, (1-((2,6-dimethyloct-7-en-2-yl)oxy)prop-1-en-2-yl)benzene, (1-((3,7-dimethyloctan-3-yl)oxy)prop-1-en-2-yl)benzene, (1-((2-methyl-1-phenylpropan-2-yl)oxy)prop-1-en-2-yl)benzene, (1-((2,6-dimethylheptan-2-yl)oxy)prop-1-en-2-yl)benzene, (2-(((Z)-hex-3-en-1-yl)oxy)vinyl)benzene, (2-phenethoxyvinyl)benzene, (2-((3,7-dimethyloct-6-en-1-yl)oxy)vinyl)benzene, (2-(octan-3-yloxy)vinyl)benzene, (2-(2-phenoxyethoxy)vinyl)benzene, (Z)-(2-(hex-3-en-1-yloxy)ethene-1,1-diyl)dibenzene, (2-phenethoxyethene-1,1-diyl)dibenzene, (1-phenethoxybut-1-en-2-yl)benzene, (3-methyl-1-phenethoxybut-1-en-2-yl)benzene, 1-methyl-4-(1-phenethoxyprop-1-en-2-yl)benzene, 1-methyl-4-(1-(octyloxy)prop-1-en-2-yl)benzene, 1-(1-(hexyloxy)prop-1-en-2-yl)-4-methylbenzene, 1-(1-(((Z)-hex-3-en-1-yl)oxy)prop-1-en-2-yl)-4-methylbenzene, 1-(1-((3,7-dimethyloct-6-en-1-yl)oxy)prop-1-en-2-yl)-4-methylbenzene, 1-methyl-4-(1-(2-phenoxyethoxy)prop-1-en-2-yl)benzene, 6-(1-phenethoxyprop-1-en-2-yl)-1,2,3,4-tetrahydronaphthalene, 6-(1-(hexyloxy)prop-1-en-2-yl)-1,2,3,4-tetrahydronaphthalene, 6-(1-(octyloxy)prop-1-en-2-yl)-1,2,3,4-tetrahydronaphthalene, 6-(1-(((Z)-hex-3-en-1-yl)oxy)prop-1-en-2-yl)-1,2,3,4-tetrahydronaphthalene, 6-(1-((3,7-dimethyloct-6-en-1-yl)oxy)prop-1-en-2-yl)-1,2,3,4-tetrahydronaphthalene, 6-(1-(2-phenoxyethoxy)prop-1-en-2-yl)-1,2,3,4-tetrahydronaphthalene, 2-(1-phenethoxyprop-1-en-2-yl)naphthalene, 2-(1-((3,7-dimethyloct-6-en-1-yl)oxy)prop-1-en-2-yl)naphthalene, 2-(1-(((Z)-hex-3-en-1-yl)oxy)prop-1-en-2-yl)naphthalene, 2-(1-(pentyloxy)prop-1-en-2-yl)naphthalene, 2-(1-(hexyloxy)prop-1-en-2-yl)naphthalene, 2-(1-(octyloxy)prop-1-en-2-yl)naphthalene, 2-(1-(2-phenoxyethoxy)prop-1-en-2-yl)naphthalene, 2-(1-(heptyloxy)prop-1-en-2-yl)naphthalene, 2-(1-(nonyloxy)prop-1-en-2-yl)naphthalene, 2-(1-(decyloxy)prop-1-en-2-yl)naphthalene, 2-(1-(octan-3-yloxy)prop-1-en-2-yl)naphthalene, 1-(1-(((Z)-hex-3-en-1-yl)oxy)prop-1-en-2-yl)-4-methoxybenzene, 1-methoxy-4-(1-(octyloxy)prop-1-en-2-yl)benzene, 1-methoxy-4-(1-phenethoxyprop-1-en-2-yl)benzene, 1-(1-(hexyloxy)prop-1-en-2-yl)-4-methoxybenzene, 1-methoxy-4-(1-(2-phenoxyethoxy)prop-1-en-2-yl)benzene, and 1-(1-((3,7-dimethyloct-6-en-1-yl)oxy)prop-1-en-2-yl)-4-methoxybenzene.

In one embodiment, at least two of the compounds of formula (II), (III) or (IV) are active compounds.

In an alternate embodiment, the compounds of formula (II), (III) or (IV) are active compounds.

According to any embodiments, the ketone or aldehyde of formula (II), the formate ester of formula (III) and the alcohol of formula (IV) are released from the precursor compound of formula (I) via oxidation of the precursor compound of formula (I) under ambient conditions. Even more, the precursor compound of formula (I) is oxidized under ambient conditions and in absence of any catalyst. For the sake of clarity, by the expression "ambient conditions", or the similar, it is meant the normal meaning understood by a person skilled in the art, i.e. the oxidation occurs at room temperature, under air, sunlight and athmospheric pressure. In other words, the environment wherein the compound is oxidized is air. Herewith it is understood, that the compound of formula (I) is oxidized in ambient air. In particular, it is understood that the compound of formula (I) does not require a pure oxygen environment, heat or catalyst to be oxidized.

Without intending to be limited to any particular theory, the rate at which the precursor compound of formula (I) is oxidized may be greater than, equal to, or slower than the evaporation rates of the individual ketone or aldehydes of formula (II), the formate esters of formula (III) or the alcohols of formula (IV).

In some embodiments, the rate at which the precursor compound of formula (I) is oxidized, and thereby, the rate at which the individual ketone or aldehydes of formula (II), the formate esters of formula (III) or the alcohols of formula (IV) are released intensifies or prolongs the diffusion effect, and/or perception of the characteristic fragrance of at least one active aldehyde or ketone formula (II), of at least one active formate ester of formula (III) and/or of at least one active alcohol of formula (IV) as defined above.

In one embodiment, 100% of the compound of formula (I) is oxidized in ambient air in a period of time ranging from 24 to 48 hours. Alternatively, 90% of the compound of formula (I) is oxidized in ambient air in a period of time ranging from 24 to 48 hours. Alternatively, 80% of the compound of formula (I) is oxidized in ambient air in a period of time ranging from 24 to 48 hours. Alternatively, 70% of the compound of formula (I) is oxidized in ambient air in a period of time ranging from 24 to 48 hours. Alternatively, 60% of the compound of formula (I) is oxidized in ambient air in a period of time ranging from 24 to 48 hours. Alternatively, 50% of the compound of formula (I) is oxidized in ambient air in a period of time ranging from 24 to 48 hours. Alternatively, 40% of the compound of formula (I) is oxidized in ambient air in a period of time ranging from 24 to 48 hours. Alternatively, 30% of the compound of formula (I) is oxidized in ambient air in a period of time ranging from 24 to 48 hours. Alternatively, 20% of the compound of formula (I) is oxidized in ambient air in a period of time ranging from 24 to 48 hours. Alternatively, 10% of the compound of formula (I) is oxidized in ambient air in a period of time ranging from 24 to 48 hours. Alternatively, 9% of the compound of formula (I) is oxidized in ambient air in a period of time ranging from 24 to 48 hours. Alternatively, 8% of the compound of formula (I) is oxidized in ambient air in a period of time ranging from 24 to 48 hours. Alternatively, 7% of the compound of formula (I) is oxidized in ambient air in a period of time ranging from 24 to 48 hours. Alternatively, 6% of the compound of formula (I) is oxidized in ambient air in a period of time ranging from 24 to 48 hours. Alternatively, 5% of the compound of formula (I) is oxidized in ambient air in a period of time ranging from 24 to 48 hours. Alternatively, 4% of the compound of formula (I) is oxidized in ambient air in a period of time ranging from 24 to 48 hours. Alternatively, 3% of the compound of formula (I) is oxidized in ambient air in a period of time ranging from 24 to 48 hours. Alternatively, 2% of the compound of formula (I) is oxidized in ambient air in a period of time ranging from 24 to 48 hours. Alternatively, 1% of the compound of formula (I) is oxidized in ambient air in a period of time ranging from 24 to 48 hours.

In one embodiment, the compound of formula (I) is encapsulated. At least one compound of formula (I) can be encapsulated in a microcapsule. In one embodiment, at least one compound of formula (I) is encapsulated in a core-shell microcapsule wherein the compound of formula (I) is contained in the core surrounded by the shell. The shell of the microcapsule protects the compound of formula (I) from the environment. The shell is made of material which is able to release the compound of formula (I) and/or the active compound of formulas (II), (III) and/or (IV). In one embodiment, the shell is made of material which is able to release the compound of formula (I) and/or the active compound of formulas (II), (III) and/or (IV) upon breakage of the shell and/or by diffusion through the shell. A person skilled in the art is well aware of processes to prepare said microcapsules.

The nature of the polymeric shell from the microcapsules of the invention can vary. As non-limiting examples, the shell can be aminoplast-based, polyurea-based or polyurethane-based. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to another embodiment the shell is polyurea-based made from, for example but not limited to isocyanate-based monomers and amine-containing crosslinkers such as guanidine carbonate and/or guanazole. Preferred polyurea microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). According to another embodiment, the emulsifier is an anionic or amphiphilic biopolymer preferably chosen from the group consisting of gum Arabic, soy protein, gelatin, sodium caseinate and mixtures thereof.

According to another embodiment, the shell is polyurethane-based made from, for example but not limited to polyisocyanate and polyols, polyamide, polyester, etc.

The preparation of an aqueous dispersion/slurry of core-shell microcapsules is well known by a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo.

U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together
- a) a polyamine component in the form of melamine or of a mixture of melamine and at least one $C_1$-$C_4$ compound comprising two $NH_2$ functional groups;
- b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
- c) a protic acid catalyst;

2) preparing an oil-in-water dispersion, wherein the droplet size is comprised between 1 and 600 um, and comprising:
  i. an oil;
  ii. a water medium
  iii. at least an oligomeric composition as obtained in step 1;
  iv. at least a cross-linker selected amongst
  A) $C_4$-$C_{12}$ aromatic or aliphatic di-or tri-isocyanates and their biurets, triurets, trimmers, trimethylol propane-adduct and mixtures thereof; and/or
  B) a di-or tri-oxiran compounds of formula
     A-(oxiran-2-ylmethyl)$_n$
     wherein n stands for 2 or 3 and 1 represents a $C_2$-$C_6$ group optionally comprising from 2 to 6 nitrogen and/or oxygen atoms;
  v. optionally a $C_1$-$C_4$ compounds comprising two $NH_2$ functional groups;
3) Heating said dispersion;
4) Cooling said dispersion.

This process is described in more details in WO 2013/068255, the content of which is included by reference.

According to another embodiment, the shell of the microcapsule is polyurea-or polyurethane-based. Examples of processes for the preparation of polyurea and polyureathane-based microcapsule slurry are for instance described in WO2007/004166, EP 2300146, EP2579976 the contents of which is also included by reference. Typically a process for the preparation of polyurea or polyurethane-based microcapsule slurry include the following steps:
- a) Dissolving at least one polyisocyanate having at least two isocyanate groups in an oil to form an oil phase;
- b) Preparing an aqueous solution of an emulsifier or colloidal stabilizer to form a water phase;
- c) Adding the oil phase to the water phase to form an oil-in-water dispersion, wherein the mean droplet size is comprised between 1 and 500 μm, preferably between 5 and 50 μm;
- d) Applying conditions sufficient to induce interfacial polymerisation and form microcapsules in form of a slurry.

In some aspects, encapsulation of a compound of formula (I) may provide an environment within the capsule wherein all, or a portion of the compound of formula (I) may oxidize, thereby releasing the individual ketone or aldehydes of formula (II), the formate esters of formula (III) or the alcohols of formula (IV) into the capsule. In some embodiments, the shell of the microcapsule may act as a permeability barrier, preventing the leakage of the individual ketone or aldehydes of formula (II), the formate esters of formula (III) or the alcohols of formula (IV) from the capsule.

Examples of microcapsules suitable for use in the present invention include, but are not limited to the microcapsules disclosed in International Patent Application Publication No. WO 2007/026307 A2. Further examples include the microcapsules disclosed in International Patent Application Publication No. WO 2014/029695 A1. Additional examples include the microcapsules disclosed in International Patent Application Publication No. WO 2006/006003 A1. Additional examples include the microcapsules disclosed in International Patent Application Publication No. WO 2006/018964 A1. Additional examples include the microcapsules disclosed in International Patent Application Publication No. WO 2007/096790 A1. Additional examples include the microcapsules disclosed in International Patent Application Publication No. WO 2009/153695 A1. Additional examples include the microcapsules disclosed in European Patent No. EP2379047.

Examples of methods to encapsulate the compound of formula (I) include, but are not limited to the microcapsules disclosed in International Patent Application Publication No. WO 2007/026307 A2. Further examples include the microcapsules disclosed in International Patent Application Publication No. WO 2014/029695 A1. Additional examples include the microcapsules disclosed in International Patent Application Publication No. WO 2006/006003 A1. Additional examples include the microcapsules disclosed in International Patent Application Publication No. WO 2006/018964 A1. Additional examples include the microcapsules disclosed in International Patent Application Publication No. WO 2007/096790 A1. Additional examples include the microcapsules disclosed in International Patent Application Publication No. WO 2009/153695 A1. Additional examples include the microcapsules disclosed in European Patent No. EP2379047.

Another object of the present invention is a method or a process to confer, enhance, improve or modify the odor properties of a perfuming composition, the air surrounding the perfuming composition, a surface, or of a perfumed article, comprising adding to the composition or article or contacting or treating the surface with an effective amount of at least one compound of formula (I) as defined above. The term "surface", as used herein may refer to a user's skin, hair, a textile, or hard surface, on to which, a perfume composition comprising or containing at least one compound of formula (I) is applied.

Another object of the present invention is a method for intensifying or prolonging the diffusion effect, and/or perception of the characteristic fragrance of at least one active aldehyde or ketone formula (II), of at least one active formate ester of formula (III) and/or of at least one active alcohol of formula (IV) as defined above, on a surface, wherein the surface is treated with at least one compound of formula (I) as defined above, or with a composition or article containing at least one compound of formula (I), under conditions susceptible of allowing the release of at least one active aldehyde or ketone formula (II), of at least one active formate ester of formula (III) and/or of at least one active alcohol of formula (IV) over time.

Moreover, the present invention relates to a perfuming composition comprising i) at least one compound of formula (I), as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di-or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture threof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

The term "perfumery base" is understood as a composition comprising at least one perfuming co-ingredient.

The perfuming co-ingredient is not a compound according to the invention. Moreover, the term "perfuming co-ingredient" is understood as a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpene hydrocarbons, nitrogenous or sulphurous heterocyclic compounds and essential oils, and the perfuming co-ingredients can be of natural or synthetic origin.

In particular one may cite perfuming co-ingredients knows for having a similar olfactive note, such as:

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propano ate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-diméthyléthyl)-1-cyclohexyl acetate, verdyl isobutyrate and/or mixture of methylionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

A perfumery base according to the invention may not be limited to the above mentioned perfuming co-ingredients, and many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

The term "perfumery adjuvant" is understood as an ingredient capable of imparting additional added benefit such as a color, a particular light resistance, chemical stability and etc. A detailed description of the nature and type of adjuvant commonly used in perfuming bases cannot be exhaustive, but it has to be mentioned that the ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidants, heat/light and or buffers or chelating agents, such as BHT), coloring agents (e.g. dyes and/or pigments), preservatives (e.g. antibacterial or antimicrobial or antifungal or anti-irritant agents), abrasives, skin cooling agents, fixatives, insect repellants, ointments, vitamins and mixture thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one of the invention's compounds of formula (I) and at least one perfumery carrier represents a particular embodiment of the invention as well as a perfuming composition comprising at least one of the invention's compounds, at least one perfumery carrier, at least one perfumery base, and optionally at least one perfumery adjuvant.

It is useful to mention here that the possibility to have, in the compositions mentioned above, more than one of the invention's compounds or other precursors of similar type is important as it enables the perfumer to prepare accords, perfumes, possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as the mixture does not provide the inventive compound in a suitable form for perfumery. Thus, unpurified reaction mixtures are generally excluded from the present invention unless otherwise specified.

Furthermore, the invention's compounds can also be advantageously used in all the fields of modern perfumery, i.e. fine or functional perfumery, to positively impart or modify the odor of a consumer product into which the compound (I) is added. Therefore, the present invention also relates to a perfumed consumer product comprising at least one compound of formula (I), as defined above or a perfuming composition as defined above.

For the sake of clarity, it has to be mentioned that, the term "perfumed consumer product" is understood as a consumer product which is expected to deliver at least a pleasant perfuming effect to the surface to which it is applied (e.g. skin, hair, textile, or hard surface). In other words, a perfumed consumer product according to the invention is a perfumed consumer product which comprises the functional formulation, as well as optionally additional benefit agents, corresponding to the desired consumer product, e.g. a conditioner, a detergent or an air freshener, and an olfactively effective amount of at least one invention's compound. For the sake of clarity, the perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of the product.

In one embodiment, the perfumed consumer product is a perfume, a fabric care product, a body-care product, a cosmetic preparation, a skin-care product, an air care product or a home care product.

Non-limiting examples of suitable perfumed consumer products include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtaincare product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Typical examples of fabric detergents or softener compositions into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullmann's Encyclopedia of Industrial Chemistry, Vol. 20, Wiley-VCH, Weinheim, p. 355-540 (2012); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the compounds according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 10% by weight, or even more, of the compounds of the invention based on the weight of the composition into which they are incorporated. Concentrations lower than these, such as in the order of 0.001% to 5% by weight, can be used when these compounds are applied directly in the perfuming or flavoring of the various consumer products mentioned hereinabove.

Moreover, the present invention relates to a compound of formula (I)

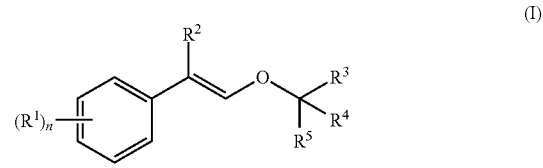

wherein n represent an integer between 0 and 5;
$R^1$, simultaneously or independently, represents at least one substituent of the aromatic ring and are a hydroxyl group, a $C_{1-6}$ alkyl group, a $C_{1-6}$ alkoxy group or a RCOO, a ROCO group wherein R is a hydrogen atom or a $C_{1-4}$ alkyl group; or two adjacent $R^1$, when taken together, represent a —O—$(CH_2)_m$—O— wherein m is 1 or 2 or form a $C_{5-10}$ saturated or unsaturated ring optionally substituted by one or more than one hydroxyl group, one or more than one $C_{1-3}$ alkyl group and/or one or more than one $C_{1-3}$ alkoxy group;
$R^2$ represents a hydrogen atom, a $C_{1-6}$ alkyl group;
$R^3$ represents a $C_{4-10}$ linear, branched or cyclic alkyl, alkenyl or alkadienyl group, a benzyl or a $C_{7-16}$ arylalkyl group optionally substituted by a hydroxyl, a $C_{1-3}$ alkyl or a $C_{1-3}$ alkoxy group, a phenoxymethyl group or a $C_{8-15}$ saturated or unsaturated alicyclic group comprising optionally an ether functional group; $R^4$ and $R^5$ represent, simultaneously or independently, a hydrogen atom or a $C_{1-6}$ alkyl group or a $C_{2-6}$ alkenyl group; or $R^3$ and $R^4$ represent, when taken together $C_{5-12}$ linear or branched alkanediyl or alkenediyl group or a $C_{5-12}$ alicyclic group.
provided that (2-((3-methylbut-2-en-1-yl)oxy)vinyl)benzene, (1-(isopentyloxy)prop-1-en-2-yl)benzene, (2-(pentyloxy)vinyl)benzene, (1-(dodecyloxy)prop-1-en-2-yl)benzene, (2-(hexyloxy)vinyl)benzene, (2-(heptyloxy)vinyl)benzene, (2-(octyloxy)vinyl) benzene, (1-(2-cyclohexylethoxy)prop-1-en-2-yl) benzene 2-(3,7-dimethylocta-2,6-dien-1-yl)oxy)vinyl) benzene, (2-phenethoxyvinyl)benzene (2-(cyclohexyloxy)vinyl)benzene, 1-(2-(cyclohexyloxy) vinyl)-4-methoxybenzene (1-(2-cyclohexylethoxy) prop-1-en-2-yl)benzene and 1-methyl-4-(1-((2-phenylcyclohexyl)oxy)prop-1-en-2-yl)benzene are excluded.

Exemplary embodiments of compounds of formula (I) are as described above.

The present invention also relates to the use of at least one compound of formula (I)

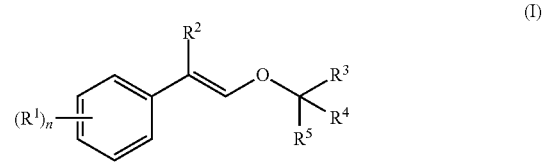

wherein n, $R^1$, $R^2$, $R^3$, $R^4$ and $R^5$ have the same meaning as defined above to release compounds selected from the group consisting of
a) a ketone or aldehyde of formula

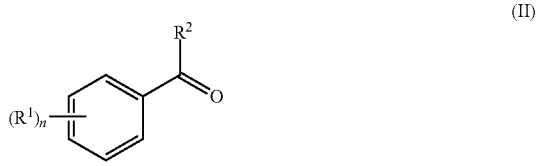
(II)

wherein n represent an integer between 0 and 5;
$R^1$, simultaneously or independently, represents at least one substituent of the aromatic ring and are a hydroxyl group, a $C_{1-6}$ alkyl group, a $C_{1-6}$ alkoxy group or a RCOO, a ROCO group wherein R is a hydrogen atom or a $C_{1-4}$ alkyl group; or two adjacent $R^1$, when taken together, represent a —O—$(CH_2)_m$—O— wherein m is 1 or 2 or form a $C_{5-10}$ saturated or unsaturated ring optionally substituted by one or more than one hydroxyl group, one or more than one $C_{1-3}$ alkyl group and/or one or more than one $C_{1-3}$ alkoxy group;
$R^2$ represents a hydrogen atom, a $C_{1-6}$ alkyl group or a $C_{6-10}$ aromatic group optionally substituted by a hydroxyl group, a $C_{1-3}$ alkyl group, a $C_{1-3}$ alkoxy group, a RCOO or a ROCO group wherein R is, independently from each other, a hydrogen atom or a $C_{1-4}$ alkyl group;
b) a formate ester of formula

(III)

wherein $R^3$, $R^4$ and $R^5$ represent, simultaneously or independently, a hydrogen atom, or a $C_{1-18}$ hydrocarbon group optionally comprising one to three oxygen atoms; or $R^3$ and $R^4$, represent, when taken together, a $C_{3-18}$ hydrocarbon group optionally comprising one to three oxygen atoms; and
c) an alcohol of formula

(IV)

wherein $R^3$, $R^4$ and $R^5$ have the same meaning as defined above;
wherein at least one of the compounds of formula (II), (III) or (IV) is an active compound upon exposure to an environment wherein the compound is oxidized, i.e. ambient conditions.

In one embodiment, the present invention relates to the use of at least one compound of formula (I) as defined above to confer, enhance, improve or modify the odor properties of a perfuming composition, the air surrounding the perfuming composition, a surface, or of a perfumed article, comprising adding to the composition or article or contacting or treating the surface with an effective amount of at least one compound of formula (I) as defined above. The term "surface", as used herein may refer to a user's skin, hair, a textile, or hard surface, on to which, a perfume composition comprising or containing the at least one compound of formula (I) is applied.

In an alternate embodiment, the present invention relates to the use of at least one compound of formula (I) as defined above for intensifying or prolonging the diffusion effect, and/or perception of the characteristic fragrance of at least one active aldehyde or ketone formula (II), of at least one formate ester of formula (III) and/or of at least one alcohol of formula (IV) as defined above, on a surface, wherein the surface is treated with at least one compound of formula (I) as defined above, or with a composition or article containing the at least one compound of formula (I), under conditions susceptible of allowing the release of the at least one aldehyde or ketone formula (II), of at least one formate ester of formula (III) and/or of at least one active alcohol of formula (IV) over time.

In some aspects, the embodiments of the uses correspond to the embodiments of the methods according to the present invention.

EXAMPLES

1. Preparation of the Compounds

The following compounds have been prepared and characterized. Mass spectral data (EI, 70 eV), major fragments ions and relative abundance, and NMR data are provided for only the E-isomer (generally the major isomer). NMR spectra were recorded at 500 or 600 MHz for $^1$H using $CDCl_3$ as solvent. The chemical displacements δ are indicated in ppm with respect to TMS as standard, and the coupling constants J are expressed in Hz.

Example 1. (1-(octyloxy)prop-1-en-2-yl)benzene: A mixture of hydratropic aldehyde (10 g, 74.5 mmol), octanol (24.3 g, 186 mmol), TsOH (0.28 g, 1.49 mmol) and toluene (100 mL) was heated at reflux for 1 h while removing the water of reaction with a Dean-Stark trap. After the mixture cooled, it was diluted with EtOAc and washed with sat. $NaHCO_3$ and sat. NaCl. The organic phase was dried with $Na_2SO_4$, filtered and concentrated to afford the crude dioctyl acetal. About a quarter of this material (19.3 mmol) was mixed with $KHSO_4$ (0.5 g, 3.67 mmol) and heated under vacuum (30 Torr) using a Kugelrohr distillation apparatus. After 2.5 h at 140° C. and another 2.5 h at 160° C., GC analysis showed that the majority of the acetal had been converted to the enol ether. Kugelrohr distillation (145° C., 80 mTorr) afforded 3.46 g of the enol ether (14.0 mmol, 73% yield) as a colorless liquid (E/Z=81:19).

$^1$H NMR ($CDCl_3$, 500 MHz, E-isomer): δ 0.88 (t, J=7.1 Hz, 3H), 1.21-1.44 (m, 10H), 1.66 (pentet, J=6.7 Hz, 2H), 2.00 (d, J=1.3 Hz, 3H), 3.83 (t, J=6.7 Hz, 2H), 6.46 (q, J=1.3 Hz, 1H), 7.12-7.17 (m, 1H), 7.24-7.32 (m, 4H).

Examples 2-7. Using a Kugelrohr distillation apparatus, a mixture of the dimethyl acetal of hydratropic aldehyde (4 g, 22.1 mmol), an alcohol (66 mmol), and $KHSO_4$ (33 mg, 0.22 mmol) was heated under vacuum (100-300 Torr) at 100-120° C. for 1-2 h to effect exchange of the methoxy groups with the alcohol while removing the liberated methanol. Following this, the temperature was increased (120-140° C.) and the pressure reduced (25-50 mTorr) to finish the elimination reaction forming the enol ether while removing the excess alcohol. The enol ether then was distilled (160-180° C., 25-50 mTorr) from the reaction mixture. If necessary, the product was further purified by a second Kugelrohr distillation.

Example 2. (1-(((Z)-hex-3-en-1-yl)oxy)prop-1-en-2-yl)benzene: Starting from (Z)-3-hexen-1-ol, the title compound was isolated as a colorless oil in 37% yield (E/Z=80:20).

$^1$H NMR (CDCl$_3$, 500 MHz, E-isomer): δ 0.97 (t, J=7.5 Hz, 3H), 1.99 (d, J=1.3 Hz, 3H), 2.07 (pentet, J=7.3 Hz, 2H), 2.41 (q, J=7.0 Hz, 2H), 3.83 (t, J=7.0 Hz, 2H), 5.33-5.40 (m, 1H), 5.47-5.54 (m, 1H), 6.46 (q, J=1.3 Hz, 1H), 7.12-7.17 (m, 1H), 7.24-7.32 (m, 4H).

Example 3. (1-(decyloxy)prop-1-en-2-yl)benzene: Starting from decanol, the title compound was isolated as a colorless oil in 75% yield (E/Z=81:19).

$^1$H NMR (CDCl$_3$, 500 MHz, E-isomer): δ 0.88 (t, J=7.0 Hz, 3H), 1.20-1.43 (m, 14H), 1.66 (pentet, J=6.8 Hz, 2H), 2.00 (d, J=1.4 Hz, 3H), 3.82 (t, J=6.7 Hz, 2H), 6.46 (q, J=1.4 Hz, 1H), 7.12-7.17 (m, 1H), 7.23-7.32 (m, 4H).

Example 4. (1-phenethoxyprop-1-en-2-yl)benzene: Starting from 2-phenylethanol, the title compound was isolated as a colorless oil in 66% yield (E/Z=81:19).

$^1$H NMR (CDCl$_3$, 600 MHz, E-isomer): δ 1.98 (d, J=1.4 Hz, 3H), 2.96 (t, J=7.0 Hz, 2H), 4.03 (t, J=7.0 Hz, 2H), 6.44 (q, J=1.4 Hz, 1H), 7.13-7.18 (m, 1H), 7.19-7.31 (m, 9H).

Example 5. (1-((3,7-dimethyloct-6-en-1-yl)oxy)prop-1-en-2-yl)benzene: Starting from citronellol, the title compound was isolated as a colorless oil in 64% yield (E/Z=83:17).

$^1$H NMR (CDCl$_3$, 500 MHz, E-isomer): δ 0.93 (d, J=6.7 Hz, 3H), 1.15-1.24 (m, 1H), 1.32-1.41 (m, 1H), 1.44-1.52 (m, 1H), 1.57-1.64 (m, 1H), 1.60 (s, 3H), 1.68 (d, J=1.3 Hz, 3H), 1.68-1.76 (m, 1 H), 1.92-2.07 (m, 2H), 1.99 (d, J=1.3 Hz, 3H), 3.82-2.92 (m, 2H), 5.10 (t, J=7.4 Hz, 1H), 6.46 (q, J=1.3 Hz, 1H), 7.12-7.17 (m, 1H), 7.23-7.33 (m, 4H).

Example 6. (1-(2-phenoxyethoxy)prop-1-en-2-yl)benzene: Starting from 2-phenoxyethan-1-ol, the title compound was isolated as a white solid in 77% yield (E/Z=80:20).

$^1$H NMR (CDCl$_3$, 500 MHz, E-isomer): δ 1.99 (d, J=1.4 Hz, 3H), 4.1 (s, 4H), 6.53 (q, J=1.4 Hz, 1H), 6.87-6.96 (m, 3H), 7.13-7.18 (m, 1H), 7.22-7.31 (m, 6H).

Example 7. (1-41-((1RS,6SR)-2,2,6-trimethylcyclohexyl)hexan-3-yl)oxy)prop-1-en-2-yl)benzene: Starting from 1-((1RS,6SR)-2,2,6-trimethylcyclohexyl)hexan-3-ol (Norlimbanol®, Firmenich) the title compound was isolated as a colorless oil in 35% yield (E/Z=83:17).

$^1$H NMR (CDCl$_3$, 500 MHz, E-isomer): δ 0.47-0.056 (m, 1H), 0.73-0.96 (Me signals, 13H), 1.00-1.74 (m, 14H), 2.00 (s, vinyl Me, 3H), 3.58-3.71 (m, 1H), 6.52 (s, 1H), 7.11-7.16 (m, 1H), 7.23-7.31 (m, 4H).

Examples 8-14. A toluene solution (100 ml) of hydratropic aldehyde (5 g, 37.3 mmol), an alcohol (0.5-2 equiv) and TsOH (142 mg, 0.75 mmol) was refluxed for 2 h. The water of reaction was removed with a Dean-Stark trap. Heating the mixture was stopped and then Na$_2$CO$_3$ (0.7 g, 6.6 mmol) was added. The reaction mixture was diluted with EtOAc and washed with water, sat. NaHCO$_3$ and brine. The organic phase was dried with Na$_2$SO$_4$, filtered and concentrated. Unless otherwise noted, the residue was subjected to Kugelrohr distillation to first remove the excess alcohol (typical conditions, 70-80° C., 20 mTorr) and then to obtain the enol ether (typical conditions, 120-140° C., 20 mTorr).

Example 8. (1-(hexyloxy)prop-1-en-2-yl)benzene: Starting from hexanol (0.5 equiv), the title compound was isolated as a colorless oil in 58% yield (E/Z=85:15) by silica gel flash chromatography (hexane) followed by Kugelrohr distillation.

$^1$H NMR (CDCl$_3$, 500 MHz, E-isomer): δ 0.90 (t, J=7.0 Hz, 3H), 1.26-1.44 (m, 6H), 1.66 (pentet, J=6.8 Hz, 2H), 2.00 (d, J=1.4 Hz, 3H), 3.83 (t, J=6.8 Hz, 2H), 6.46 (q, J=1.4 Hz, 1H), 7.12-7.17 (m, 1H), 7.24-7.32 (m, 4H).

Example 9. (1-(benzyloxy)prop-1-en-2-yl)benzene: Starting from benzyl alcohol (0.9 equiv), the title compound was isolated as a colorless oil in 54% yield (E/Z=83:17) by silica gel flash chromatography (hexane) followed by Kugelrohr distillation.

$^1$H NMR (CDCl$_3$, 500 MHz, E-isomer): δ 2.04 (d, J=1.4 Hz, 3H), 4.86 (s, 2H), 6.53 (q, J=1.4 Hz, 1H), 7.11-7.16 (m, 1H), 7.21-7.36 (m, 9H).

Example 10. (1-(octan-3-yloxy)prop-1-en-2-yl)benzene: Starting from 3-octanol (2 equiv), the title compound was isolated as a colorless oil in 75% yield (E/Z=85:15).

$^1$H NMR (CDCl$_3$, 500 MHz, E-isomer): δ 0.89 (t, J=7.0 Hz, 3H), 0.94 (t, J=7.5 Hz, 3H), 1.23-1.64 (m, 10 H), 2.00 (d, J=1.3 Hz, 3H), 3.62 (pentet, J=6.0 Hz, 1H), 6.52 (q, J=1.3 Hz, 1H), 7.10-7.15 (m, 1H), 7.22-7.32 (m, 4H).

Example 11. (1-(((1R,2S,5R)-2-isopropyl-5-methylcyclohexyl)oxy)prop-1-en-2-yl)benzene: Starting from (−)-menthol (2 equiv), the title compound was isolated as a colorless oil in 86% yield (E/Z=88:12).

$^1$H NMR (CDCl$_3$, 500 MHz, E-isomer): δ 0.81 (d, J=7.0 Hz, 3H), 0.86-0.93 (m, 1H), 0.92 (d, J=6.6 Hz, 3H), 0.93 (d, J=7.0 Hz, 3H), 0.97-1.11 (m, 2H), 1.34-1.46 (m, 2H), 1.63-1.70 (m, 2H), 1.99 (d, J=1.3 Hz, 3H), 2.02-2.10 (m, 1H), 2.14-2.24 (m, 1H), 3.50 (dt, J=4.3, 10.7 Hz, 1H), 6.56 (q, J=1.3 Hz, 1H), 7.11-7.16 (m, 1H), 7.24-7.32 (m, 4H).

Example 12. ((2-phenylprop-1-en-1-yl)oxy)cyclododecane: Starting from cyclododecanol (1 equiv), the title compound was isolated as a white solid in 47% yield (E/Z=85:15) by silica gel flash chromatography (hexane).

$^1$H NMR (CDCl$_3$, 500 MHz, E-isomer): δ 1.26-1.51 (m, 18H), 1.54-1.63 (m, 2H), 1.69-1.79 (m, 2H), 1.99 (d, J=1.3 Hz, 3H), 3.86 (m, 1H), 6.52 (q, J=1.3 Hz, 1H), 7.12-7.16 (m, 1H), 7.24-7.32 (m, 4H).

Example 13. (1-(1-(3,3-dimethylcyclohexyl)ethoxy)prop-1-en-2-yl)benzene: Starting from 1-(3,3-dimethylcyclohexyl)ethan-1-ol (1 equiv), the title compound was isolated as a colorless oil in 84% yield (E/Z=88:12).

$^1$H NMR (CDCl$_3$, 500 MHz, E-isomer): δ 0.90 (s, 3H), 0.92 (s, 3H), 0.92-1.12 (m, 3H), 1.19 (d, J=6.4 Hz, 3H), 1.31-1.84 (m, 6H), 2.00 (d, J=1.3 Hz, 3H), 3.58 (pentet, J=6.2 Hz, 1H), 6.49 (q, J=1.3 Hz, 1H), 7.12-7.16 (m, 1H), 7.23-7.32 (m, 4H).

Example 14.: Starting from 1-((2-(tert-butyl)cyclohexyl)oxy)butan-2-ol (1 equiv), the title compound was isolated as a colorless oil in 56% yield (mixture of diastereomers).

$^1$H NMR (CDCl$_3$, 500 MHz, E-isomer, 4 diastereomers): δ 0.90, 0.92, 0.94, 0.97 (all s, 9H), 0.95-1.02 (m, 4), 1.04-1.84 (m, 9H), 1.97-2.00 (overlapping Me signals, 3H), 1.99-2.15 (m, 1H), 3.01-3.11, 3.25-3.40, 3.51-3.83 (all m, 4H), 6.55, 6.57, 6.60, 6.66 (all q, J=1.3 Hz, 1H), 7.10-7.16 (m, 1H), 7.22-7.32 (m, 4H).

Examples 15-18. A pentane solution (100 ml) of hydratropic aldehyde (5 g, 37.2 mmol), a tertiary alcohol (74.4 mmol) and TsOH (0.28 g, 1.47 mmol) was heated at reflux for 22 h. The water of reaction was removed with a Dean-Stark trap. Heating the mixture was stopped and Na$_2$CO$_3$ (0.7 g, 6.6 mmol) was added. The reaction mixture was diluted with EtOAc and washed with water, sat. NaHCO$_3$, and brine. The organic phase was dried with Na$_2$SO$_4$, filtered and concentrated. The residue was subjected to Kugelrohr distillation first to remove the excess tertiary alcohol and then the enol ether.

Example 15. (1-((2,6-dimethyloct-7-en-2-yl)oxy)prop-1-en-2-yl)benzene: Starting from 2,6-dimethyloct-7-en-2-ol (dihydromyrcenol), the title compound was isolated as a colorless oil in 81% yield (E/Z=85:15).

¹H NMR (CDCl₃, 500 MHz, E-isomer): δ 0.98 (d, J=6.7 Hz, 3H), 1.22-1.32 (m, 2H), 1.28 (s, 6H), 1.32-1.43 (m, 2H), 1.51-1.60 (m, 2H), 1.99 (d, J=1.4 Hz, 3H), 2.12 (m, 1H), 4.90 (ddd, J=0.9, 1.9, 10.3 Hz, 1H), 4.95 (ddd, J=1.3, 1.9, 17.3 Hz, 1H), 5.68 (ddd, J=7.5, 10.3 17.3 Hz, 1H), 6.66 (q, J=1.4 Hz, 1H), 7.12-7.17 (m, 1H), 7.24-7.33 (m, 4H).

Example 16. (1-((3,7-dimethyloctan-3-yl)oxy)prop-1-en-2-yl)benzene: Starting from 3,7-dimethyloctan-3-ol (tetrahydrolinalool), the title compound was isolated as a colorless oil in 74% yield (E/Z=87:13).

¹H NMR (CDCl₃, 500 MHz, E-isomer): δ 0.87 (d, J=6.7 Hz, 6H), 0.9 (t, J=7.5 Hz, 3H), 1.17 (m, 2H), 1.23 (s, 3H), 1.34 (m, 2H), 1.48-1.67 (m, 5H), 2.00 (d, J=1.3 Hz, 3H), 6.65 (q, J=1.3 Hz, 1H), 7.09-7.16 (m, 1H), 7.23-7.33 (m, 4H).

Example 17. (1-((2-methyl-1-phenylpropan-2-yl)oxy)prop-1-en-2-yl)benzene: Starting from 2-methyl-1-phenylpropan-2-ol, the title compound was isolated as a colorless oil in 63% yield (E/Z=87:13).

¹H NMR (CDCl₃, 500 MHz, E-isomer): δ 1.28 (s, 6H), 2.00 (d, J=1.4 Hz, 3H), 2.88 (s, 2H), 6.75 (q, J=1.4 Hz, 1H), 7.12-7.33 (m, 10H).

Example 18. (1-((2,6-dimethylheptan-2-yl)oxy)prop-1-en-2-yl)benzene: Starting from 2,6-dimethylheptan-2-ol, the title compound was isolated as a colorless oil in 69% yield (E/Z=87:13).

¹H NMR (CDCl₃, 500 MHz, E-isomer): δ 0.88 (d, J=6.7 Hz, 6H), 1.14-1.20 (m, 2H), 1.29 (s, 6H), 1.34-1.42 (m, 2H), 1.50-1.59 (m, 3H), 2.00 (d, J=1.4 Hz, 3H), 6.67 (q, J=1.4 Hz, 1H), 7.12-7.18 (m, 1H), 7.24-7.33 (m, 4H).

Examples 19-21: Using a Kugelrohr distillation apparatus, a mixture of the dimethyl acetal of phenylacetaldehyde (5 g, 30.1 mmol), an alcohol (120 mmol), and KHSO₄ (51 mg, 0.375 mmol) was heated under vacuum (200-300 Torr) at 90-120° C. for 2-3 h to effect exchange of the methoxy groups with the added alcohol while removing the liberated methanol. Following this the temperature was increased (130-140° C.) and the pressure reduced (25-30 mTorr) to finish the elimination reaction forming the enol ether. Under these conditions the generated enol ether and alcohol were distilled from the reaction mixture as they formed. The distillate then was subjected to another bulb-to-bulb distillation, first removing the excess alcohol and then the enol ether.

Example 19. (2-(((Z)-hex-3-en-1-yl)oxy)vinyl)benzene: Starting from (Z)-3-hexen-1-ol, the title compound was isolated as a colorless oil in 36% yield (E/Z=55:45).

¹H NMR (CDCl₃, 500 MHz, E-isomer): δ 0.98 (t, J=7.5 Hz, 3H), 2.07 (pentet, J=7.5 Hz, 2H), 2.45 (q, J=6.9 Hz, 2H), 3.80 (t, J=6.9 Hz, 2H), 5.33-5.41 (m, 1H), 5.48-5.55 (m, 1H), 5.83 (d, J=13.0 Hz, 1H), 6.97 (d, J=13.0 Hz, 1H), 7.08-7.13 (m, 1H), 7.17-7.28 (m, 4H).

Example 20. (2-phenethoxyvinyl)benzene: Starting from 2-phenylethanol, the title compound was isolated as a colorless oil in 36% yield (E/Z=53:47).

¹H NMR (CDCl₃, 500 MHz, E-isomer): δ 2.98 (t, J=7.0 Hz, 2H), 4.00 (t, J=7.0 Hz, 2H), 5.82 (d, J=13.0 Hz, 1H), 6.96 (d, J=13.0 Hz, 1H), 7.07-7.31 (m, 10H).

Example 21. (2-((3,7-dimethyloctyl)oxy)vinyl)benzene: Starting from citronellol, the title compound was isolated as a colorless oil in 48% yield (E/Z=48:52).

¹H NMR (CDCl₃, 500 MHz, E-isomer): δ 0.94 (d, J=6.7 Hz, 3H), 1.16-1.42 (m, 1H), 1.33-1.42 (m, 1H), 1.46-1.56 (m, 1H), 1.60 (s, 3H), 1.60-1.71 (m, 1H), 1.68 (d, 1.1 Hz, 3H), 1.71-1.18 (m, 1H), 1.92-2.08 (m, 2H), 3.79-3.89 (m, 2H), 5.07-5.13 (m, 1H), 5.82 (d, J=13.0 Hz, 1H), 6.98 (d, J=13.0 Hz, 1H), 7.08-7.14 (m, 1H), 7.19-7.29 (m, 4H).

Examples 22-23. Phenylacetaldehyde dimethyl acetal (14.9 g, 90 mmol), alcohol (225 mmol), and KHSO₄ (61 mg, 0.45 mmol) were added to a 100 ml, round-bottomed flask equipped with a Vigreux column (11 cm), distillation head and nitrogen bubbler. The mixture was heated (oil bath at 150° C.) while distilling out the liberated methanol until the vapor temperature dropped (1-2 h) signaling that most of the methanol had been removed. The Vigreux column was removed. The mixture was placed under vacuum (30 mTorr) and heated (190-200° C. oil bath). The enol ether and alcohol were allowed to distill from the reaction flask as they formed. Factions rich in the enol ether were combined and distilled to afford the pure enol ethers.

Example 22. (2-(octan-3-yloxy)vinyl)benzene: Starting from 3-octanol, the title compound was isolated by fractional distillation (Vigreux column, bp 105° C., 25 mTorr) as a colorless oil in 27% yield (E/Z=37:63).

¹H NMR (CDCl₃, 600 MHz, E-isomer): δ 0.89 (t, J=7.0 Hz, 3H), 0.94 (t, J=7.5 Hz, 3H), 1.24-1.48 (m, 6H), 1.49-1.70 (m, 4H), 3.70 (pentet, J=6.1 Hz, 1H), 5.91 (d, J=12.7 Hz, 1H), 6.88 (d, J=12.7 Hz, 1H), 7.07-7.13 (m, 1H), 7.17-7.30 (m, 4H).

Example 23. (2-(2-phenoxyethoxy)vinyl)benzene: Starting from 2-phenoxyethan-1-ol, the title compound was isolated by Kugelrohr distillation (170° C., 25 mTorr) as a white solid in 46% yield (E/Z=52:48).

¹H NMR (CDCl₃, 500 MHz, E-isomer): δ 4.20 (s, 4H), 5.89 (d, J=13.0 Hz, 1H), 6.87-6.98 (m, 3H), 7.05 (d, J=13.0 Hz, 1H), 7.10-7.15 (m, 1H), 7.20-7.31 (m, 6H).

Example 24. (Z)-(2-(hex-3-en-1-yloxy)ethene-1,1-diyl)dibenzene: The dimethyl acetal of diphenylacetaldehyde was prepared by mixing the aldehyde (14.1 g, 71.6 mmol) with trimethyl orthoformate (3 equiv), TsOH (1.2 mole %) and methanol (100 mL) for 17 h. The acid was neutralized by adding Na₂CO₃ (2.5 g). After concentrating, the remaining residue was subjected to a short-path distillation (105-108° C., 25 mTorr) affording 15 g (62 mmol, 86% yield) of the dimethyl acetal. The acetal (5.81 g, 24 mmol) then was combined with Z-hex-3-en-1-ol (2 equiv) and KHSO₄ (1 mole %) in a round-bottomed flask (15 mL) equipped with a distillation head and nitrogen bubbler. The mixture was heated (oil bath at 150° C.) while distilling out the liberated methanol for 1 h. The mixture then was placed under vacuum (7 Torr) and heated at 180° C. while allowing the excess alcohol to distill from the flask (2 h). Na₂CO₃ (0.5 g) was added and 5.5 g (19.8 mmol, 82% yield) of the title compound was isolated as a colorless oil by distillation from the reaction flask (bp 152-155° C., 25 mTorr).

¹H NMR (CDCl₃, 600 MHz): δ 0.95 (t, J=7.5 Hz, 3H), 2.06 (pentet, J=7.5 Hz, 2H), 2.45 (q, J=7.1 Hz, 2H), 3.91 (t, J=7.0 Hz, 2H), 5.36 (dt, J=7.3, 10.8 Hz, 1H), 5.52 (dt, J=7.3, 10.8 Hz, 1H), 6.49 (s, 1H), 7.18-7.24 (m, 4H), 7.25-7.32 (m, 4H), 7.39-7.42 (m, 2H).

Example 25. (2-phenethoxyethene-1,1-diyl)dibenzene: A mixture of diphenylacetaldehyde (4.94 g, 25.2 mmol), 2-phenylethanol (7.78 g, 64 4 mmol), TsOH (0.097 g, 0.51 mmol) and toluene (100 mL) was heated at reflux for 2 h while removing the water of reaction with a Dean-Stark trap. After the mixture cooled, it was diluted with EtOAc and washed with sat. NaHCO₃ and water. The organic phase was dried with Na₂SO₄, filtered and concentrated. The crude acetal then was mixed with KHSO₄ (1 g, 7.34 mmol) and heated under vacuum (50 Torr) using a Kugelrohr distillation apparatus. After 1 h at 160° C., GC analysis showed that the majority of the acetal had been converted to the enol ether and the excess 2-phenylethanol removed. Kugelrohr distillation (180-190° C., 50 mTorr) afforded 4.24 g of the title compound (14 1 mmol, 56% yield) as a colorless liquid.

$^1$H NMR (CDCl$_3$, 500 MHz): δ 2.97 (t, J=7.0 Hz, 2H), 4.09 (t, J=7.0 Hz, 2H), 6.45 (s, 1H), 7.14-7.35 (m, 15H).

Examples 26-29. Methoxymethyltriphenylphosphonium chloride (15.1 g, 44.1 mmol) and the aryl ketone (29.4 mmol) were added to 120 ml of toluene. Potassium t-butoxide (5.27g, 47 mmol) was added to the stirring slurry in 4 portions every 15 min. The mixture was stirred for 4 h becoming a deep red color. It then was poured into 500 ml of water and extracted with EtOAc (3×250 mL). The organic phases were combined, dried over Na$_2$SO$_4$, filtered and concentrated. The resulting methyl enol ether product was isolated by flash chromatography (silica gel, hexane) followed by Kugelrohr distillation. The methyl enol ether (30 mmol) then was combined with 2-phenylethanol (2 equiv) and KHSO$_4$ (1 mole %) in a round-bottomed flask (15 mL) equipped with a distillation head and nitrogen bubbler. The mixture was heated (oil bath at 150° C.) while distilling out the liberated methanol (vapor temperature 64° C.) until the vapor temperature dropped (typically 40 min). The mixture then was placed under vacuum (300 mTorr) and heated at 190° C. while allowing the excess 2-phenylethanol to distill from the flask (typically 2 h). The resulting enol ethers were isolated by vacuum distillation from the reaction flask after adding Na$_2$CO$_3$ (0.4 g) or by silica gel flash chromatography followed by Kugelrohr distillation.

Example 26. 1-methyl-4-(1-phenethoxyprop-1-en-2-yl) benzene: The title compound was isolated by short-path distillation of the crude reaction mixture (bp 143-145° C., 30 mTorr) as a colorless oil in 73% yield (E/Z=82:18) from the methyl enol ether.

$^1$H NMR (CDCl$_3$, 600 MHz, E-isomer): δ 1.97 (d, J=1.2 Hz, 3H), 2.31 (s, 3H), 2.97 (t, J=7.1 Hz, 2H), 4.03 (t, J=7.1 Hz, 2H), 6.42 (q, J=1.2 Hz, 1H), 7.07-7.32 (m, 9H).

Example 27. 1-methoxy-4-(1-phenethoxyprop-1-en-2-yl) benzene: The title compound was isolated by short-path distillation of the crude reaction mixture (bp 156-158° C., 30 mTorr) as a white solid in 84% yield (E/Z=78:23) from the methyl enol ether.

$^1$H NMR (CDCl$_3$, 600 MHz, E-isomer): δ 1.96 (d, J=1.2 Hz, 3H), 2.98 (t, J=7.1 Hz, 2H), 3.78 (s, 3H), 4.03 (t, J=7.1 Hz, 2H), 6.36 (q, J=1.2 Hz, 1H), 6.81-6.85 (m, 2H), 7.18-7.32 (m, 7H).

Example 28. 2-(1-phenethoxyprop-1-en-2-yl)naphthalene: The title compound was isolated by flash chromatography followed by Kugelrohr distillation affording a white solid in 89% yield (E/Z=80:20) from the methyl enol ether.

$^1$H NMR (CDCl$_3$, 600 MHz, E-isomer): δ 2.09 (d, J=1.2 Hz, 3H), 3.00 (t, J=7.0 Hz, 2H), 4.10 (t, J=7.0 Hz, 2H), 6.62 (q, J=1.2 Hz, 1H), 7.19-7.48 (m, 8H), 7.64 (s, 1H), 7.72 (d, J=8.7 Hz, 1H), 7.74-7.78 (m, 2H).

Example 29. 6-(1-phenethoxyprop-1-en-2-yl)-1,2,3,4-tetrahydronaphthalene: The title compound was isolated by flash chromatography followed by Kugelrohr distillation affording a colorless oil in 82% yield (E/Z=80:20) from the methyl enol ether.

$^1$H NMR (CDCl$_3$, 600 MHz, E-isomer): δ 1.75-1.81 (m, 4H), 1.96 (d, J=1.3 Hz, 3H), 2.70-2.78 (m, 4H), 2.97 (t, J=7.1 Hz, 2H), 4.03 (t, J=7.1 Hz, 2H), 6.40 (q, J=1.3 Hz, 1H), 6.95-7.03 (m, 3H), 7.20-7.33 (m, 5H).

Example 30. (1-phenethoxybut-1-en-2-yl)benzene: The methyl enol ether of 2-phenylbutanal, prepared from propiophenone as described for Examples 26-29, and 2-phenylethanol were used to prepare the title compound in 59% yield by the procedure described for Examples 2-7. It was isolated by Kugelrohr distillation as a colorless oil in 59% yield (E/Z=74:26).

$^1$H NMR (CDCl$_3$, 500 MHz, E-isomer): δ 0.99 (t, J=7.5 Hz, 3H), 2.52 (q, J=7.5 Hz, 2H), 2.95 (t, J=7.1 Hz, 2H), 4.01 (t, J=7.1 Hz, 2H), 6.30 (s, 1H), 7.12-7.31 (m, 10H).

Example 31. (3-methyl-1-phenethoxybut-1-en-2-yl)benzene: The methyl enol ether of 3-methyl-2-phenylbutanal, prepared from isobutyrophenone as described for Examples 26-29, and 2-phenylethanol were used to prepare the title compound by the procedure described for Examples 2-7. It was isolated by silica gel flash chromatography as a colorless oil in 24% yield (E/Z=55:45).

$^1$H NMR (CDCl$_3$, 500 MHz, E-isomer): δ 1.11 (d, J=7.1 Hz, 6H), 2.95 (t, J=7.1 Hz, 2H), 3.02 (pentet, J=7.1 Hz, 1H), 3.97 (t, J=7.1 Hz, 2H), 5.98 (s, 1H), 7.10-7.31 (m, 10H).

Example 32. 1-methoxy-4-(1-(octyloxy)prop-1-en-2-yl) benzene: The methyl enol ether of 2-(4-methoxyphenyl) propanal, prepared from p-methoxyacetophenone as described for Examples 26-29, and octanol were used to prepare the title compound by the procedure described for Examples 2-7. The title compound was isolated by Kugelrohr distillation as a colorless oil in 69% yield (E/Z=76:24).

$^1$H NMR (CDCl$_3$, 500 MHz, E-isomer): δ 0.88 (t, J=7.0 Hz, 3H), 1.22-1.43 (m, 10H), 1.65 (pentet, J=6.8 Hz, 2H), 1.97 (d, J=1.3 Hz, 3H), 3.77 (s, 3H), 3.80 (t, J=6.8 Hz, 2H), 6.37 (q, J=1.3 Hz, 1H), 6.80-6.84 (m, 2H), 7.19-7.24 (m, 2H).

Example 33. 2-(14(3,7-dimethyloct-6-en-1-yl)oxy)prop-1-en-2-yl)naphthalene: The methyl enol ether of 2-(naphthalen-2-yl)propanal (25.2 mmol), prepared from 1-(naphthalen-2-yl)ethan-1-one as described for Examples 26-29 was combined with citronellol (2 equiv) and KHSO$_4$ (1 mole %) in a round-bottomed flask equipped with a distillation head. The vessel was place under vacuum (25 mbar) and heated at 150° C. for 30 min while distilling out the liberated methanol. After reducing the vacuum to 1 Torr, the mixture was heated for 90 min at 165° C. while allowing the excess citronellol to distill from the flask. The reaction mixture was diluted with CH$_2$Cl$_2$ and then washed with sat. Na$_2$CO$_3$. The organic phase was dried with Na$_2$SO$_4$, filtered and concentrated. The residue was subjected to silica gel flash chromatography (hexane/EtOAc, 98:2) affording 5.23 g (16.2 mmol, 64% yield) of the title compound as a pale yellow oil (E/Z=88:22).

$^1$H NMR (CDCl$_3$, 500 MHz, E-isomer): δ 0.95 (d, J=6.6 Hz, 3H), 1.15-1.27 (m, 1H), 1.34-1.43 (m, 1H), 1.45-1.56 (m, 1H), 1.61-1.67 (m, 1H), 1.61 (s, 3H), 1.68 (s, 3H), 1.70-1.79 (m, 1 H), 1.93-2.08 (m, 2H), 2.10 (d, J=1.3 Hz, 3H), 3.86-2.98 (m, 2H), 5.11 (t, J=7.1 Hz, 1H), 6.65 (q, J=1.3 Hz, 1H), 7.34-7.45 (m, 2H), 7.49 (dd, J=8.7, 1.9 Hz, 1H), 7.67 (s, 1H), 7.72 (d, J=8.7 Hz, 1H), 7.74-7.80 (m, 2H).

2. Headspace Analysis from Fabric Softener Application

A model liquid fabric softener was prepared by mixing a TEA-esterquat (Stepantex® VL 90A), 12.3 wt %, 10% aqueous calcium chloride, 0.4 wt %, Proxcel GXL, 0.04 wt % and deionized water, 87.2 wt %. The enol ethers (0.075 mmol) were weighed into a vial and dissolved in 0.25 mL of acetone. Liquid fabric softener (4.5 g) was added to the vial and the mixture shaken by hand to mix. Reference samples were prepared in the same manner using 0.075 mmol of each released volatile. The fabric softener samples were rinsed with deionized water into a 3 L beaker and the beaker was filled to a total volume of 1.5 L. Three, 5-g cotton swatches (ca. 12.5×12.5 cm, weight 270 g/m$^2$, item 403 from Testfabrics, West Pittston, Pa.) were added to the beaker and agitated by hand for 3 min. After an additional 2 min of standing, the swatches were removed and excess water squeezed out by hand. The cloths were hung to dry overnight (15-16 h) at rt. The swatches then were subjected to dynamic headspace analysis.

Each swatch was placed inside a thermostatted (25° C.), headspace sampling cell (about 160 mL volume). Using an air-sampling pump, a constant flow of air (200 mL/min) was drawn through the sampling cell and then through a cartridge containing 100 mg of Tenax® (the waste cartridge). Prior to entering the sample cell, the air was drawn through a plug of active charcoal and then through a saturated NaCl solution to maintain a constant relative humidity of 75%. Headspace samples were collected after 1 and 2 hours by replacing the waste cartridge with a clean Tenax® cartridge for 15 min. The cartridges were thermally desorbed with a Perkin Elmer TurboMatrix 650 thermal desorber coupled to an Agilent 6890 gas chromatograph equipped with an Agilent 5975C mass spectrometer and a Varian VF-1 ms capillary column (30 m, i.d. 0.25 mm, film 0.25 μm). The desorber parameters were: valve temperature 250° C., transfer line 250° C., purge time 1 min, desorption temperature 240° C., desorption time 5 min, desorption flow 20 mL/min, trap −30° C. to 250° C. at 40° C./sec, trap hold time 4 min, outlet split 48 mL/min, column flow 1 mL/min. The GC oven temperature profile was 60° C. (1 min) to 210° C. at 20° C./min then ramped to 250° C. (2 min). When analysing for (Z)-3-hexen-1-ol the initial oven temperature was 52° C. (2 min). The amount of each fragrance volatile collected (reported as ng/L of air) was determined using external standard calibrations of the respective chemicals. At least five acetone solutions were prepared with concentrations of the analytes ranging from 0.05 g/L to 5 g/L. The solutions were injected (0.2 μL) onto Tenax® cartridges and desorbed as described above. Each solution was analyzed in triplicate. Calibration curves were forced through the origin.

Dynamic headspace concentrations (ng/L) of perfumery raw materials obtained from line-dried cotton treated with fabric softener containing enol ether profragrances compared to their respective references (data for the 60-75 and 120-135 min headspace samples).

|  |  | 60 min sample | | 120 min sample | |
| --- | --- | --- | --- | --- | --- |
|  |  | profragrance | reference | profragrance | reference |
| Ex. 2 | acetophenone | 377 (±118) | 1.4 (±0.5) | 329 (±28.9) | 1.2 (±0.3) |
|  | (Z)-3-hexen-1-yl formate | 140 (±22.4) | 2.3 (±0.5) | 128 (±15.1) | 3.3 (±1.9) |
|  | (Z)-3-hexen-1-ol | 117 (±24.9) | 2.8 (±0.5) | 131 (±13.8) | 2.6 (±0.6) |
| Ex. 4 | acetophenone | 258 (±54) | 1.6 (±0.6) | 267 (±80.2) | 1.4 (±0.6) |
|  | 2-phenylethyl formate | 341 (±50) | 0.4 (±0.1) | 336 (±126) | 0.4 (±0.1) |
|  | 2-phenylethanol | 18.1 (±0.6) | 24.8 (±2.6) | 26.7 (±1.7) | 35.3 (±4.4) |
| Ex. 5 | acetophenone | 460 (±27) | 1.6 (±0.6) | 306 (±56.2) | 1.4 (±0.6) |
|  | citronellyl formate | 277 (±2.9) | 2.9 (±1.7) | 232 (±21.7) | 5 (±0.1) |
|  | citronellol | 42.1 (±29.8) | 29.8 (±2.5) | 58.3 (±6.9) | 29.8 (±4.6) |
| Ex. 10 | acetophenone | 360 (±25.5) | 2.7 (±0) | 367 (±51.8) | 2.3 (±0.2) |
|  | 3-octyl formate | 253 (±11.2) | 6.3 (±1.3) | 221 (±4.3) | 8.4 (±2.6) |
|  | 3-octanol | 161 (±13.0) | 1.1 (±0.3) | 213 (±16.9) | 1.2 (±0.1) |
| Ex. 13 | acetophenone | 196 (±20.1) | 1.5 (±0.2) | 231 (±12.9) | 2.1 (±1.3) |
|  | 1-(3,3-dimethylcyclohexyl)ethyl formate | 101 (±7.4) | 1.9 (±0.3) | 118 (±10.1) | 2.2 (±0.8) |
|  | 1-(3,3-dimethylcyclohexyl)ethan-1-ol | 30.9 (±3.5) | 2.1 (±0.7) | 50.4 (±0.9) | 3.1 (±0.6) |
| Ex. 15 | acetophenone | 135 (±48.7) | 1.7 (±0.3) | 140 (±41.7) | 1.6 (±0.1) |
|  | dihydromyrcenol formate | 104 (±30.7) | 3.5 (±3.0) | 125 (±18.4) | 2.9 (±1.2) |
|  | dihyromyrcenol | 72.9 (±25.6) | 0.6 (±0.2) | 101 (±42.8) | 0.8 (±0.5) |
| Ex. 16 | acetophenone | 139 (±18.6) | 2.5 (±0.8) | 109 (±13.7) | 1.5 (±0.3) |
|  | tetrahydrolinalyl formate | 118 (±9.3) | 4.6 (±2.0) | 123 (±3.3) | 3.8 (±0.8) |
|  | tetrahydrolinalool | 79.7 (±14.4) | 1.8 (±0.7) | 106 (±19.8) | 1.3 (±0.3) |
| Ex. 19 | benzaldehyde | 157 (±68.6) | 2.4 (±0.6) | 147 (±25.1) | 2.4 (±0.5) |
|  | (Z)-3-hexen-1-yl formate | 110 (±26.5) | 2.3 (±0.5) | 112 (±7.5) | 3.3 (±1.9) |
|  | (Z)-3-hexen-1-ol | 71 (±36.4) | 2.8 (±0.7) | 90 (±32.5) | 2.6 (±0.6) |
| Ex. 20 | benzaldehyde | 304 (±72.5) | 2.4 (±0.6) | 243 (±60.3) | 2.4 (±0.5) |
|  | 2-phenylethyl formate | 319 (±119) | 0.4 (±0.1) | 294 (±167) | 0.4 (±0.1) |
|  | 2-phenylethanol | 53.7 (±3.7) | 24.8 (±2.6) | 58.7 (±27.4) | 35.3 (±4.4) |
| Ex. 21 | benzaldehyde | 411 (±116) | 1.2 (±0.1) | 309 (±44.1) | 1.3 (±0.3) |
|  | citronellyl formate | 342 (±112) | 2.2 (±1.7) | 300 (±103) | 5.0 (±0.1) |
|  | citronellol | 51.4 (±5.5) | 27.9 (±2.5) | 66.7 (±10.8) | 29.8 (±4.6) |
| Ex. 24 | benzophenone | 157 (±6.4) | 96.7 (±27.5) | 168 (±14.6) | 150 (±30.7) |
|  | (Z)-3-hexenyl formate | 240 (±18.6) | not detected | 180 (±5.7) | not detected |
|  | (Z)-3-hexen-1-ol | 181 (±63.3) | 2.9 (±0.2) | 198 (±50.5) | not detected |
| Ex. 26 | p-methylacetophenone | 674 (±196) | 1.8 (±0.1) | 603 (±128) | 2.8 (±0.1) |
|  | 2-phenylethyl formate | 706 (±186) | 1.0 (±0.5) | 494 (±84.4) | 1.1 (±0.4) |
|  | 2-phenylethanol | 139 (±23.8) | 44.3 (±13.1) | 163 (±38.8) | 91.9 (±17.9) |
| Ex. 27 | p-methoxyacetophenone | 115 (±14.9) | 2.9 (±0.6) | 112 (±16.8) | 5.3 (±0.1) |
|  | 2-phenylethyl formate | 330 (±110) | 0.9 (±0.2) | 281 (±37.1) | 2.0 (±1.5) |
|  | 2-phenylethanol | 147 (±22.6) | 20.2 (±4.4) | 161 (±30.5) | 33.0 (±2.1) |
| Ex. 28 | methyl naphthyl ketone | 60.4 (±5.4) | 19.0 (±2.3) | 60.1 (±11.1) | 30.4 (±1.3) |
|  | 2-phenylethyl formate | 211 (±14.0) | 0.9 (±0.3) | 155 (±10.0) | 2.0 (±1.9) |
|  | 2-phenylethanol | 41.3 (±3.5) | 26.5 (±5.7) | 50.3 (±6.0) | 43.4 (±2.7) |

These data indicate that, when applied to cotton fabric from a fabric softener application, the compounds of formula (I) release considerable more perfumery ingredients (aryl carbonyl compounds, formate esters and alcohols) than the corresponding reference samples. This demonstrates that the compounds of the invention produced the desired slow-release effect.

3. Olfactive Evaluation with a Leave-On Hair Conditioner

A model rinse-off hair conditioner was prepared with following composition (weight %):

| | |
|---|---|
| Deionized water | 95.50% |
| Salcare SC 91 (origin: BASF) | 1.00% |
| Aculyn ™ 46 (origin: Dow) | 1.00% |
| Wacker-Belsil ® DMS 6038 (origin: Wacker) | 0.50% |
| Phenonip ™ (origin: Clariant) | 0.50% |
| Mirasil ® ADM-E (origin: Elkem) | 1.50% |

A 25% enol ether solution in isopropyl myrisate or a 25% enol ether solution in acetone was dispersed in a leave-on hair conditioner to provide samples containing 0.15 wt % or 0.25 wt % of the precursor, respectively. Reference samples containing an equimolar level of the expected aldehyde or ketone and formate ester were prepared in the same way. The samples were left macerating at room temperature for one day. The hair swatches (10 g) were rinsed under warm tap water (37° C.) for 30 s then gently combed to straighten the hair. The hair conditioner samples (1 g) were each applied to a swatch and then massaged into the hair to disperse it thoroughly. The swatches were hung and allowed to dry at room temperature. They were olfactively evaluated by a panel for odor intensity after 6 and 24 h. Panelists were asked to rate the perceived odor intensity on a scale ranging from 1 (imperceptible) to 7 (very intense). The data obtained from the panel evaluations are summarized in Table 1.

TABLE 1

Olfactive Evaluation with a Leave-on Hair Conditioner

| Tested molecule (wt % in conditioner) | Mean Odor Intensity (# of panelists) | |
|---|---|---|
| Reference materials | 6 hours | 24 hours |
| Example 2 (0.25%) | 4.3 (16) | 3.1 (23) |
| acetophenone (Z)-3-hexen-1-yl formate | 2.3 (16) | 1.7 (23) |
| Example 5 (0.25%) | 4.0 (16) | 3.5 (23) |
| acetophenone citronellyl formate | 2.8 (16) | 1.7 (23) |
| Example 4 (0.25%) | 4.6 (12) | 3.9 (13) |
| acetophenone 2-phenylethyl formate | 2.5 (12) | 1.3 (13) |
| Example 19 (0.25%) | 5.2 (17) | 2.9 (12) |
| benzaldehyde (Z)-3-hexen-1-yl formate | 2.1 (17) | 2.5 (12) |
| Example 20 (0.25%) | 3.9 (17) | 3.7 (13) |
| benzaldehyde 2-phenylethyl formate | 1.8 (17) | 1.7 (13) |
| Example 28 (0.15%) | 5.5 (25) | 4.8 (22) |
| methylnapthyl ketone 2-phenylethyl formate | 3.3 (25) | 2.3 (22) |
| Example 33 (0.15%) | 5.7 (17) | 5.7 (19) |
| methylnapthyl ketone citronellyl formate | 2.8 (17) | 3.6 (19) |

These data suggest that the compounds of formula (I) produced a higher odor intensity on hair than the corresponding reference samples at both 6 h and 24 h after application from a leave-on hair conditioner. This demonstrates that the compounds of the invention produced the desired slow-release effect.

4. Olfactive Evaluation with a Rinse-Off Hair Conditioner

A model rinse-off hair conditioner was prepared with following composition (weight %)

| | |
|---|---|
| Deionized water | 92.54% |
| Chlorhexidine dihydrochloride | 0.05% |
| Natrosol ® 250 H (origin: Hercules) | 1.00% |
| Dehyquart ® C 4046 (origin: Cognis) | 0.20% |
| Mirasil ® ADM-E (origin: Rhodia) | 1.20% |
| Genamin ® KDM (origin: Clariant) | 1.00% |
| Crodamol ® SS (origin: Croda) | 0.50% |
| Crodacol ® C90 (origin: Croda) | 3.01% |
| Myristyl alcohol (origin: Aldrich) | 0.20% |
| Nipagin ® M (origin: Nipa) | 0.30% |

A 25% enol ether solution in isopropyl myrisate was dispersed in a rinse-off hair condition to provide a conditioner containing 0.25 or 0.15 wt % of the precursor. A reference sample containing an equimolar level of the expected aldehyde or ketone and formate ester was prepared in the same way. The samples were left macerating at room temperature for one day. Hair swatches (10 g) were wetted with warm tap water (about 37° C.) and washed with an unperfumed milky shampoo. The shampoo (1 mL) was applied with a syringe along the length of each hair swatch. The swatches were massaged with fingertips for 30 s to distribute the shampoo and develop a good lather. They were rinsed with warm tap water for 30 s and the excess water gently squeezed out. The rinse-off conditioner (1.0 g) was applied along the hair swatch and gently massaged into the hair for 1 min. The swatch was then dipped in a 2-L beaker of warm tap water and moved up and down three times and then side-to-side three times. It then was rinse for 30 s with tap water while detangling the hair with fingertips. After gently squeezing out excess water, the swatches were hung and allowed to dry at room temperature. The swatches were olfatively evaluated by a panel for odor intensity after 6 and 24 h. Panelists were asked to rate the perceived odor intensity on a scale ranging from 1 (imperceptible) to 7 (very intense). The data obtained from the panel evaluation are summarized in Table 2.

TABLE 2

Olfactive Evaluation with a Rinse-off Hair Conditioner

| Tested molecule (wt % in conditioner) | Mean Odor Intensity (# of panelists) | |
|---|---|---|
| Reference materials | 6 hours | 24 hours |
| Example 2 (0.25%) | 4.6 (19) | 3.5 (26) |
| acetophenone (Z)-3-hexen-1-yl formate | 3.7 (19) | 1.9 (26) |
| Example 5 (0.25%) | 4.0 (17) | 4.5 (12) |
| acetophenone citronellyl formate | 3.1 (17) | 2.7 (12) |
| Example 4 (0.25%) | 3.9 (17) | 2.0 (19) |
| acetophenone 2-phenylethyl formate | 3.2 (17) | 1.8 (19) |
| Example 28 (0.15%) | 4.3 (15) | 3.6 (17) |
| methylnapthyl ketone 2-phenylethyl formate | 1.5 (15) | 1.7 (17) |
| Example 33 (0.15%) | 5.0 (20) | 5.1 (18) |
| methylnapthyl ketone citronellyl formate | 1.9 (20) | 2.2 (18) |

These data suggest that the compounds of formula (I) produced a higher odor intensity on hair than the corresponding reference samples at both 6 h and 24 h after application from a rinse-off hair conditioner. This demonstrates that the compounds of the invention produced the desired slow-release effect.

5. Olfactive Evaluation in Pearly Shampoo

A model pearly shampoo was prepared in a generally known manner with following composition (weight %)

| Deionized water | 46.27% |
|---|---|
| EDETA B Powder (origin: BASF) | 0.05% |
| Jaguar C14 S ® (origin: Rhodia) | 0.05% |
| UCare ™ Polymer JR-400 (origin: Dow) | 0.075% |
| 10% NaOH solution | 0.30% |
| Sulfetal LA B-E (origin: Z&H Handel) | 34.00% |
| Zetesol LA ® (origin: Z&H Handel) | 9.25% |
| Tego ® Betaine F 50 (origin: Evonik) | 2.00% |
| Xiameter ® MEM-1691 (origin: Dow Corning) | 2.50% |
| Cetyl alcohol | 1.20% |
| Comperlan 100 (origin: BTC Speciality Techn.) | 1.50% |
| Cutina ® AGS (origin: BASF) | 2.00% |
| Kathon ™ CG (origin: Dow) | 0.10% |
| Panthenol 75% (origin: BASF) | 0.10% |
| Sodium Chloride 25% | 0.60% |

A 25% enol ether solution in isopropyl myrisate was dispersed in a pearly shampoo to provide samples containing 0.15 wt % of the precursor. A reference sample containing an equimolar level of the expected ketone and formate ester was prepared in the same way. The samples were left macerating at room temperature for one day. Hair swatches (10 g) were wetted with warm tap water (about 37° C.) and washed with milky shampoo. The shampoo (1 gram) was applied with a syringe along the length of each hair swatch. The swatches were massaged with fingertips for 30 s to distribute the shampoo and develop a good lather. They were rinsed with warm tap water for 30 s and the excess water gently squeezed out. The swatches then were washed again with the pearly shampoo for 30 sec and rinsed for 30 sec with warm tap water. After gently squeezing out excess water, the swatches were hung and allowed to dry at room temperature. The swatches were olfactively evaluated by a panel for odor intensity after 6 and 24 h. Panelists were asked to rate the perceived odor intensity on a scale ranging from 1 (imperceptible) to 7 (very intense). The data obtained from the panel evaluation are summarized in Table 3.

TABLE 3

Olfactive Evaluation in Pearly Shampoo

| Tested molecule (wt % in shampoo) | Mean Odor Intensity (# of panelists) | |
|---|---|---|
| Reference materials | 6 hours | 24 hours |
| Example 5 (0.15%) | 2.0 (16) | not determined |
| acetophenone | 1.3 (16) | not determined |
| citronellyl formate | | |
| Example 21 (0.15%) | 2.8 (16) | 2.2 (16) |
| benzaldehyde | 1.8 (16) | 1.9 (16) |
| citronellyl formate | | |
| Example 28 (0.15%) | 3.8 (21) | 2.5 (17) |
| methylnapthyl ketone | 2.5 (21) | 2.0 (17) |
| 2-phenylethyl formate | | |
| Example 33 (0.15%) | 2.7 (19) | 3.5 (15) |
| methylnapthyl ketone | 1.5 (19) | 1.8 (15) |
| citronellyl formate | | |

These data suggest that the compounds of formula (I) produced a higher odor intensity on hair than the corresponding reference samples at both 6 h and 24 h after application from a shampoo. This demonstrates that the compounds of the invention produced the desired slow-release effect.

6. Olfactive Evaluation with an Antiperspirant/Deodorant Stick

A model antiperspirant was prepared in a generally known manner with following composition (weight %)

| Dow Corning 345 Fluid | 55.00% |
|---|---|
| Lanette ® 18 (origin: BASF) | 21.00% |
| Tegosoft ® PBE (origin: Evonik) | 2.00% |
| Cutina ® HR (origin: BASF) | 1.00% |
| Summit ® AZP-908 (origin: SummitReheis) | 20.00% |

A sample containing 0.15 wt % of an enol ether profragrance was prepared by dispersing a 15:20 mixture of the enol ether and isopropyl myrisate in the molten antiperspirant composition. A reference sample containing an equimolar level of the expected ketone and formate ester was prepared in the same way. The molten samples were poured into deodorant stick molds and left macerating at room temperature for one day. An amount of 0.25 g of each sample was spread evenly on paper blotters of 4.5 cm×12 cm. The blotters were stored under ambient conditions for 6 and 24 h. The blotters were olfactively evaluated by a panel for odor intensity after 6 and 24 h. Panelists were asked to rate the perceived odor intensity on a scale ranging from 1 (imperceptible) to 7 (very intense). The data obtained from the panel evaluations are summarized in Table 4.

TABLE 4

Olfactive Evaluation with an Antiperspirant/Deodorant Stick

| Tested molecule (wt % in AP/Deo Stick) | Mean Odor Intensity (# of panelists) | |
|---|---|---|
| Reference materials | 6 hours | 24 hours |
| Example 2 (0.15%) | 3.4 (19) | 1.5 (20) |
| acetophenone | 1.3 (19) | 1.4 (20) |
| (Z)-3-hexen-1-yl formate | | |
| Example 4 (0.15%) | 4.3 (22) | 1.5 (18) |
| acetophenone | 1.6 (22) | 1.4 (18) |
| 2-phenylethyl formate | | |
| Example 5 (0.15%) | 3.4 (18) | 1.3 (18) |
| acetophenone | 2.1 (18) | 1.5 (18) |
| citronellyl formate | | |
| Example 19 (0.15%) | 2.2 (17) | 1.4 (25) |
| benzaldehyde | 1.3 (17) | 1.3 (25) |
| (Z)-3-hexen-1-yl formate | | |
| Example 20 (0.15%) | 3.9 (14) | 2.9 (19) |
| benzaldehyde | 1.5 (14) | 1.6 (19) |
| 2-phenylethyl formate | | |
| Example 27 (0.15%) | 3.9 (15) | not determined |
| p-methoxyacetophenone | 1.9 (15) | not determine |
| 2-phenylethyl formate | | |

These data suggest that the compounds of formula (I) produced higher odor intensities on blotters than the corresponding reference samples 6 h after application from an antiperspirant stick. This demonstrates that the compounds of the invention produced the desired slow-release effect.

7. Olfactive Evaluation in an Eau de Toilette

A 1% solution of the enol ether in ethanol 40B and water (85:15 by weight) was prepared. A reference sample containing an equimolar level of the expected ketone and formate ester was prepared. If a mixture did not become homogeneous, both the enol ether and corresponding reference sample were sonicated in a 25° C. water bath for 10-20 min. 20 µl of each solution was applied to the center of 4.5 cm×12 cm paper blotter. The blotters were stored under ambient conditions for 3 and 6 h. The blotters were olfactively evaluated by a panel of 20-25 people for odor intensity after 6 and 24 h. Panelists were asked to rate the perceived odor intensity on a scale ranging from 1 (imperceptible) to 7 (very intense). The data obtained from the panel evaluations are summarized in Table 5.

TABLE 5

Olfactive Evaluation in an Eau de Toilette

| Tested molecule (wt % in eau de toillete) | Mean Odor Intensity (# of panelists) | |
|---|---|---|
| Reference materials | 3 hours | 6 hours |
| Example 2 (1%) | 3.4 (20) | 2.1 (20) |
| acetophenone | 1.6 (20) | 1.7 (20) |
| (Z)-3-hexen-1-yl formate | | |
| Example 4 (1%) | 4.0 (21) | 3.5 (21) |
| acetophenone | 2.0 (21) | 1.4 (21) |
| 2-phenylethyl formate | | |
| Example 5 (1%) | 3.3 (22) | 2.6 (22) |
| acetophenone | 1.6 (22) | 1.2 (22) |
| citronellyl formate | | |
| Example 19 (1%) | 2.2 (22) | 1.9 (22) |
| benzaldehyde | 1.4 (22) | 1.1 (22) |
| (Z)-3-hexen-1-yl formate | | |
| Example 20 (1%) | 4.6 (16) | 3.2 (16) |
| benzaldehyde | 1.6 (16) | 1.5 (16) |
| 2-phenylethyl formate | | |
| Example 21 (1%) | 2.7 (22) | 1.8 (22) |
| benzaldehyde | 1.3 (22) | 1.6 (22) |
| citronellyl formate | | |
| Example 27 (1%) | 3.8 (22) | 2.7 (22) |
| p-methoxyacetophenone | 2.4 (22) | 2.0 (22) |
| 2-phenylethyl formate | | |

These data suggest that the compounds of formula (I) produced higher odor intensities on blotters than the corresponding reference samples 3 h and 6 h after application from an ethanolic solution. This demonstrates that the compounds of the invention produced the desired slow-release effect.

8. Preparation of a Liquid Detergent Comprising the Invention's Compound

TABLE 6

Composition of the liquid detergent formulation

| Ingredients | Concentration [wt %] |
|---|---|
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Properase L[4] | 0.2 |
| Puradax EG L[4] | 0.2 |
| Purastar ST L[4] | 0.2 |
| Acrylates/Steareth-20 Methacrylate structuring Crosspolymer[5] | 6 |
| Deionized Water | 27.4 |

[1] Hostapur SAS 60; Origin: Clariant
[2] Edenor K 12-18; Origin: Cognis
[3] Genapol LA 070; Origin: Clariant
[4] Origin: Genencor International
[5] Aculyn 88; Origin: Dow Chemical The liquid detergent is prepared by adding 0.01 to 0.5% by weight, relative to the total weight of the liquid detergent, of the invention's compounds of example 20, 28 or 33 into the unperfumed liquid detergent formulation of Table 6 under gentle shaking.

9. Preparation of a Transparent isotropic Shampoo Comprising the Invention's Composition

TABLE 7

Composition of the transparent isotropic shampoo formulation

| Phases | Ingredients | Concentration [wt %] |
|---|---|---|
| A | Water deionized | 44.4 |
| | Polyquaternium-10 [1] | 0.3 |
| | Glycerin 85% [2] | 1 |
| | DMDM Hydantoin [3] | 0.2 |
| B | Sodium Laureth Sulfate [4] | 28 |
| | Cocamidopropyl Betaine [5] | 3.2 |
| | Disodium Cocoamphodiacetate [6] | 4 |
| | Ethoxy (20) Stearyl Alcohol [6] | 1 |
| C | Sodium Laureth Sulfate [4] | 3 |
| | Glyceryl Laureate [7] | 0.2 |
| D | Water deionized | 1 |
| | Sodium Methylparaben [8] | 0.1 |
| E | Sodium Chloride 10% aqueous sol. | 15 |
| | Citric acid 10% aqueous sol. till pH 5.5-6 | q.s. |

[1] Ucare Polymer JR-400, Origin: Noveon
[2] Origin: Schweizerhall
[3] Glydant, Origin: Lonza
[4] Texapon NSO IS, Origin: Cognis
[5] Tego Betain F 50, Origin: Evonik
[6] Amphotensid GB 2009, Origin: Zschimmer & Schwarz
[7] Monomuls 90 L-12, Origin: Gruenau
[8] Nipagin Monosodium, Origin: NIPA The shampoo is prepared by dispersed in water Polyquaternium-10. The remaining ingredients of phase A are mixed separately by addition of one after the other while mixing well after each adjunction. This pre-mix is added to the Polyquaternium-10 dispersion and mixed for another 5 min. Then, the premixed phase B and the premixed Phase C are added (Monomuls 90L-12 is heated to melt in Texapon NSO IS) while agitating. Phase D and Phase E are added while agitating. pH is adjusted with citric acid solution till pH: 5.5-6.0 leading to an unperfumed shampoo formulae.

The perfumed shampoo is prepared by adding 0.01 to 0.5% by weight, relative to the total weight of the shampoo, of the invention's compound of example 20, 28 or 33 into the unperfumed shampoo formulation of Table 7 under gentle shaking.

10. Preparation of a Structured Shower Gel Comprising the Invention's Composition

TABLE 8

Composition of the shower gel formulation

| Ingredients | Amount (% wt) |
|---|---|
| WATER deionised | 49.350 |
| Tetrasodium EDTA [1] | 0.050 |
| Acrylates Copolymer[2] | 6.000 |
| Sodium C12-C15 Pareth Sulfate [3] | 35.000 |
| Sodium Hydroxide 20% aqueous solution | 1.000 |
| Cocamidopropyl Betaine[4] | 8.000 |

TABLE 8-continued

Composition of the shower gel formulation

| Ingredients | Amount (% wt) |
|---|---|
| Methylchloroisothiazolinone and Methylisothiazolinone[5] | 0.100 |
| Citric Acid (40%) | 0.500 |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS The shower gel is prepared by adding 0.01 to 0.5% by weight, relative to the total weight of the shower gel, of the invention's compound of example 20, 28 or 33 into the unperfumed shower gel formulation of Table 8 under gentle shaking.

11. Preparation of a Transparent Shower Gel Comprising the Invention's Composition

TABLE 9

Composition of the transparent shower gel formulation

| Ingredients | Concentration (% wt) |
|---|---|
| WATER deionized | 52.40 |
| Tetrasodium EDTA [1] | 0.10 |
| Sodium Benzoate | 0.50 |
| Propylene Glycol | 2.00 |
| Sodium C12-C15 Pareth Sulfate [2] | 35.00 |
| Cocamidopropyl Betaine[3] | 8.00 |
| Polyquaternium-7[4] | 0.20 |
| Citric Acid (40%) | 1.00 |
| Sodium Chloride | 0.80 |

[1] EDETA B POWDER; trademark and origin: BASF
[2] ZETESOL AO 328 U; trademark and origin: ZSCHIMMER & SCHWARZ
[3] TEGO-BETAIN F 50; trademark and origin: GOLDSCHMIDT
[4] MERQUAT 550; trademark and origin: LUBRIZOL The transparent shower gel is prepared by adding 0.01 to 0.5% by weight, relative to the total weight of the shower gel, of the invention's compound of example 20, 28 or 33 into the unperfumed shower gel formulation of Table 9 under gentle shaking.

12. Preparation of a Milky Shower Gel Comprising the Invention's Composition

TABLE 10

Composition of the milky shower gel formulation

| Ingredients | Concentration (% wt) |
|---|---|
| WATER deionized | 50.950 |
| Tetrasodium EDTA [1] | 0.050 |
| Sodium Benzoate | 0.500 |
| Glycerin 86% | 3.500 |
| Sodium Laureth Sulfate [2] | 27.000 |
| Polyquaternium-7[3] | 1.000 |
| Coco-Betaine[4] | 6.000 |
| PEG-120 Methyl Glucose trioleate[5] | 1.000 |
| Citric Acid (40%) | 1.000 |
| Glycol Distearate & Laureth-4 & Cocamidopropyl Betaine[6] | 3.000 |

TABLE 10-continued

Composition of the milky shower gel formulation

| Ingredients | Concentration (% wt) |
|---|---|
| Sodium Chloride 20% | 5.000 |
| PEG-40 Hydrogenated Castor Oil[7] | 1.000 |

[1] EDETA B POWDER; trademark and origin: BASF
[2] Texapon NSO IS; trademark and origin: COGNIS
[3] MERQUAT 550; trademark and origin: LUBRIZOL
[4] DEHYTON AB-30; trademark and origin: COGNIS
[5] GLUCAMATE LT; trademark and origin: LUBRIZOL
[6] EUPERLAN PK 3000 AM; trademark and origin: COGNIS
[7] CREMOPHOR RH 40; trademark and origin: BASF The transparent shower gel is prepared by adding 0.01 to 0.5% by weight, relative to the total weight of the shower gel, of the invention's compound of example 20, 28 or 33 into the unperfumed shower gel formulation of Table 10 under gentle shaking.

13. Preparation of a Hand Dishwash Comprising the Invention's Composition

TABLE 11 composition of Hand dishwash formulation

| Ingredients | Amount (% wt) |
|---|---|
| Linear alkylbenzene sulfonic acid [1] | 20 |
| Diethanolamide [2] | 3.5 |
| Sodium Hydroxide (50%) [3] | 3.4 |
| Secondary alcohol ethoxolate [4] | 2.5 |
| Sodium xylene sulfonate | 6.3 |
| Water | 64.3 |

[1] Biosoft S-118 ®; trademark and origin: Stepan Company
[2] Ninol 40-CO ®; trademark and origin: Stepan Company
[3] Stepanate SXS ®; trademark and origin: Stepan Company
[4] Tergitol 15-S-9 ®; trademark and origin: Dow Chemical Company Water with sodium hydroxide and diethanolamide are mixed. LAS is added. After the LAS is neutralized, the remaining ingredients are added. The pH is checked (=7-8) and adjusted if necessary.

The perfumed hand dishwash is prepared by adding 0.01 to 0.5% by weight, relative to the total weight of the hand dishwash, of the invention's compound of example 20, 28 or 33 into the unperfumed hand dishwash formulation of Table 11 under gentle shaking.

14. Preparation of an All-Purpose Cleaner Comprising the Invention's Composition

TABLE 12

Composition of an all-purpose cleaner firmulation

| Ingredients | Amount (% wt) |
|---|---|
| Ethoxylated Alcohol (C9-C11, 8EO) [1] | 20 |
| Sodium Dodecyl Benzene Sulfonate [2] | 16 |
| Sodium Cumene Sulfonate [3] | 8 |

TABLE 12-continued

Composition of an all-purpose cleaner firmulation

| Ingredients | Amount (% wt) |
|---|---|
| Methyl chloro isothiazolinone Methyl isothiazolinone 3.3:1 [4] | 0.8% |
| Water | 55.9 |

[1] Neodol 91-8 ®; trademark and origin: Shell Chemical
[2] Biosoft D-40 ®; trademark and origin: Stepan Company
[3] Stepanate SCS ®; trademark and origin: Stepan Company
[4] Kathon CG ®; trademark and origin: Dow Chemical Company All ingredients were mixed together and then the mixture was diluted with water to 100%. The all-purpose cleaner is prepared by adding 0.01 to 0.5% by weight, relative to the total weight of the all-purpose cleaner, of the invention's compound of example 20, 28 or 33 into the unperfumed all-purpose cleaner formulation of Table 12 under gentle shaking.

15. Microencapsulation of the Compounds of Formula (I)

Synthesis of Microcapsules Containing Compounds of the Present Invention: In this example, the technique used to synthesize microcapsules with fragrance oil cores is the interfacial polymerization of a biopolymer-stabilized, oil-in-water emulsion with an oil soluble polyisocyanate monomer which self-polymerizes at the oil-water interface.

SuperStab AA Senegal Gum Arabic was purchased from Nexira, Somerville, N.J. Takenate® D-110N was purchased from Mitsui Chemicals, Tokyo, Japan. Desmodur N100 was obtained from Covestro (formerly Bayer Material Science), Pittsburgh, Pa. Guanidine carbonate (≥99%, 120222500) is purchased from Acros Organics, New Jersey, USA.

Microcapsules containing profragrance or the individual fragrance material components were generated by first preparing the oil and aqueous phases, as well as the guanidine carbonate crosslinker solution. The oil phase was prepared by mixing 10 g of the profragrance molecule desribed in Example 2 (or fragrance raw materials) with 2.24 g Desmodur N100 in a scintillation vial and incorporating by magnetic stir bar at room temperature until the isocyanate was completely dissolved. The aqueous phase was prepared by dissolving 0.50 g of Superstab AA powder into 33.6 g of 18.2 MΩ·cm water via magnetic stir bar at room temperature. The guanidine carbonate crosslinker solution was prepared by dissolving 0.56 g of guanidine carbonate into 3.10 g of 18.2 MΩ·cm water. The oil phase was added dropwise by pipette to the aqueous phase while emulsifying the aqueous phase using an IKA UltraTurrax homogenizing wand at 18000 rpm for 3 minutes. The emulsion was poured into a jacketed reactor and stirred by overhead stirrer at 500 rpm. The crosslinker solution was slowly auto-injected into the reactor by syringe pump at a rate of 125 µL/min until fully incorporated into the emulsion. The temperature of the reactor was increased to 50° C. over 30 minutes, then up to 70° C. over another 30 minutes. The reactor was then held at 70° C. for 4 hours and then allowed to cool to room temperature. The resulting slurry was drained into a jar.

Particle size characterizations were carried out for each slurry using a Mastersizer 3000 (Malvern Instruments Ltd., UK). The mean particle size, or D[4,3], was measured as 31.1 µm for the profragrance-containing microcapsules. Particle morphologies were characterized by a JEOL JSM-6010 PLUS scanning electron microscope (JEOL Ltd, Tokyo, Japan).

Measurements of oil loading were deduced from solids content of microcapsule slurries as characterized by thermogravimetric analysis using a TA Q50 TGA (TA Instruments, Delaware, USA). Slurries were exposed to elevated temperatures (50° C.) to evaporate as much water as possible to determine the amount of residual encapsulated oil and shell material, or solids content. Solids content was calculated as the percentage of the original mass remaining after maintaining elevated temperature for 250 minutes.

The total content of oil in the bulk slurry was determined by diluting 1 mL of the slurry in 4 mL of acetonitrile and filtering out the residual solid material with a 17 mm, 0.45 µm regenerated cellulose (RC) filter followed by a 4 mm, 0.2 µm RC filter. This solution was analyzed by GCMS and the content of individual materials determined by comparison to an external calibration curve. The oil content in the aqueous phase of the slurry was determined by isolating the aqueous phase through centrifugation of 1 mL of slurry at 10000 rpm for 5 min. The separated aqueous phase was filtered through a 17 mm, 0.45 µm RC filter followed by a 4 mm, 0.2 µm RC filter and the filtrant diluted in 4 mL of acetonitrile. This solution was analyzed by GCMS and the content of individual materials determined by comparison to an external calibration curve.

The amount of oil inside the microcapsules was defined as the difference between the two measurements (bulk slurry oil content minus the aqueous phase oil content). The encapsulation efficiency is the ratio between the amount of oil inside the microcapsules and the amount of oil loaded into the slurry during the microencapsulation process and expressed as a percentage.

| Capsule Component | Encapsulation Efficiency | | |
|---|---|---|---|
| | % Encapsulated | % Aqueous | % Total Detected |
| acetophenone | 74.78 | 3.77 | 78.55 |
| 3-hexen-1-yl formate | 70.97 | 6.81 | 77.78 |
| 3-hexen-1-ol | 57.41 | 11.60 | 69.0 |
| Ex. 2 Profragrance | 93.04 | 6.94 | 99.9 |

When analyzed by this method, the amounts of the individual raw materials, acetophenone, 3-hexen-1-yl formate and 3-hexen-1-ol were less than the amount that was initially loaded into the slurry, with only 78.55% of the acetophenone, 77.78% of the 3-hexen-1-yl formate and 69.0% of the 3-hexen-1-ol accounted for, and encapsulation efficiencies of 74.78%, 70.97% and 57.41% of the original loadings of these compounds, respectively. This poor encapsulation efficiency was not unexpected due to the low log P of each of these compounds, resulting in partitioning of these materials into the aqueous phase and the high volatility of each likely resulted in lost mass from evaporation due to the elevated temperatures present during the encapsulation reaction. The encapsulation efficiency of the profragrance at 93.04% was shown to be greater than that of the individual control materials.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method to release from a precursor compound, compounds selected from the group consisting of a) a ketone or aldehyde of formula

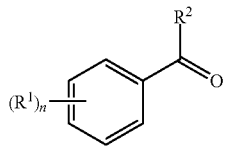

(II)

wherein n represent an integer between 0 and 5;

$R^1$, simultaneously or independently, represents at least one substituent of the aromatic ring and is a hydroxyl group, a $C_{1-6}$ alkyl group, a $C_{1-6}$ alkoxy group or a RCOO, a ROCO group wherein each R is a hydrogen atom or a $C_{1-4}$ alkyl group; or two adjacent $R^1$, when taken together, represent a —O—$(CH_2)_m$—O— group wherein m is 1 or 2, or form a $C_{5-10}$ saturated or unsaturated ring optionally substituted by one or more than one hydroxyl group, one or more than one $C_{1-3}$ alkyl group and/or one or more than one $C_{1-3}$ alkoxy group;

$R^2$ represents a hydrogen atom, a $C_{1-6}$ alkyl group or a $C_{6-10}$ aromatic group optionally substituted by a hydroxyl group, a $C_{1-3}$ alkyl group, a $C_{1-3}$ alkoxy group, a RCOO or a ROCO group, wherein each R is, independently from each other, a hydrogen atom or a $C_{1-4}$ alkyl group;

b) a formate ester of formula

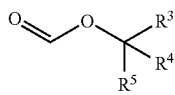

(III)

wherein $R^3$, $R^4$ and $R^5$ represent, simultaneously or independently, a hydrogen atom, or a $C_{1-18}$ hydrocarbon group optionally comprising one to three oxygen atoms; or $R^3$ and $R^4$, represent, when taken together, a $C_{3-18}$ hydrocarbon group optionally comprising one to three oxygen atoms; and c) an alcohol of formula

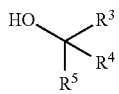

(IV)

wherein $R^3$, $R^4$ and $R^5$ have the same meaning as defined above;

wherein the precursor compound comprises a compound of formula (I)

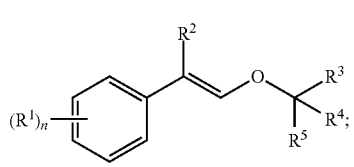

(I)

wherein n, $R^1$, $R^2$, $R^3$, $R^4$ and $R^5$ have the same meaning as defined above;

by exposing the precursor compound of formula (I) to ambient conditions in the absence of a catalyst, wherein the ambient conditions comprise room temperature, ambient air, and atmospheric pressure.

2. The method according to claim 1, wherein n is 0, 1, or 2.

3. The method according to claim 1, wherein $R^1$, simultaneously or independently, represents a hydroxyl group, a $C_{1-4}$ alkyl group or a $C_{1-3}$ alkoxy group; or two adjacent $R^1$ represent, when taken together, a —O—$CH_2$—O— group, a —$(CH_2)_4$— group, or a —$(CH)_4$— group.

4. The method according to claim 1, wherein $R^2$ represents a hydrogen atom, a $C_{1-3}$ alkyl group or a phenyl group.

5. The method according to claim 1, wherein $R^3$ represents a $C_{2-18}$ hydrocarbon group optionally comprising one to three oxygen atoms.

6. The method according to claim 1, wherein $R^3$ represents a $C_{4-10}$ linear, branched or cyclic alkyl, alkenyl or alkadienyl group, a phenyl, a benzyl, a $C_{7-16}$ arylalkyl or a styryl group optionally substituted by a hydroxyl group, a $C_{1-3}$ alkyl group or a $C_{1-3}$ alkoxy group, a phenoxymethyl group or a $C_{8-15}$ saturated or unsaturated alicyclic group comprising optionally an ether functional group; $R^4$ and $R^5$ represent, simultaneously or independently, a hydrogen atom or a $C_{1-6}$ alkyl group or a $C_{2-6}$ alkenyl group; or $R^3$ and $R^4$ represent, when taken together $C_{5-12}$ linear or branched alkanediyl or alkenediyl group or a $C_{5-12}$ alicyclic group.

7. The method according to claim 1, wherein at least one of the compounds of formula (II), (III) or (IV) is a perfuming ingredient.

8. The method according to claim 1, wherein at least two of the compounds of formula (II), (III) or (IV) are perfuming ingredients.

* * * * *